US 11,529,198 B2

United States Patent
Wu

(10) Patent No.: US 11,529,198 B2
(45) Date of Patent: *Dec. 20, 2022

(54) OPTICAL AND NON-OPTICAL SENSOR TRACKING OF OBJECTS FOR A ROBOTIC CUTTING SYSTEM

(71) Applicant: Stryker Corporation, Kalamazoo, MI (US)

(72) Inventor: Chunwu Wu, Kalamazoo, MI (US)

(73) Assignee: Stryker Corporation, Kalamazoo, MI (US)

(*) Notice: Subject to any disclaimer, the term of this patent is extended or adjusted under 35 U.S.C. 154(b) by 395 days.

This patent is subject to a terminal disclaimer.

(21) Appl. No.: 16/783,654

(22) Filed: Feb. 6, 2020

(65) Prior Publication Data

US 2020/0197105 A1 Jun. 25, 2020

Related U.S. Application Data

(63) Continuation of application No. 15/599,935, filed on May 19, 2017, now Pat. No. 10,575,906, which is a (Continued)

(51) Int. Cl.
*A61B 5/00* (2006.01)
*A61B 34/20* (2016.01)
(Continued)

(52) U.S. Cl.
CPC .............. *A61B 34/20* (2016.02); *A61B 5/064* (2013.01); *A61B 34/30* (2016.02); *A61B 90/39* (2016.02);
(Continued)

(58) Field of Classification Search
CPC ......... A61B 34/20; A61B 5/064; A61B 34/30; A61B 90/39; A61B 2034/2048;
(Continued)

(56) References Cited

U.S. PATENT DOCUMENTS 5,086,401 A 2/1992 Glassman et al.
5,279,309 A 1/1994 Taylor et al.
(Continued)

FOREIGN PATENT DOCUMENTS

CN 101267776 A 9/2008
CN 202146362 U 2/2012
(Continued)

OTHER PUBLICATIONS

A Literature Review: Robots in Medicine, Hsia, T.C.; Mittelstadt, B., Jun. 1991, vol. 10, Issue 2, pp. 13-22, 10 pages.
(Continued)

*Primary Examiner* — Joel Lamprecht
(74) *Attorney, Agent, or Firm* — Howard & Howard Attorneys PLLC

(57) ABSTRACT

Systems and methods are disclosed that utilize a robotic device supporting and moving a cutting tool in at least three degrees of freedom. A control system commands the robotic device to control or constrain movement of the cutting tool. A first tracker is coupled to the robotic device and a second tracker is coupled to an anatomy. The second tracker includes three markers that generate optical signals and a non-optical sensor that generates non-optical signals. A navigation system with an optical sensor is in communication with the control system. The navigation system receives, with the optical sensor, the optical signals from one or more of the three markers and receives the non-optical signals from the non-optical sensor. The navigation system communicates position data indicative of a position of the anatomy to the control system to control cutting of the anatomy based on the received optical and non-optical signals.

23 Claims, 9 Drawing Sheets

Related U.S. Application Data continuation of application No. 14/994,236, filed on Jan. 13, 2016, now Pat. No. 9,687,307, which is a continuation of application No. 14/635,402, filed on Mar. 2, 2015, now Pat. No. 9,271,804, which is a continuation of application No. 14/035,207, filed on Sep. 24, 2013, now Pat. No. 9,008,757.

(60) Provisional application No. 61/705,804, filed on Sep. 26, 2012.

(51) Int. Cl.
*A61B 5/06* (2006.01)
*A61B 34/30* (2016.01)
*A61B 90/00* (2016.01)

(52) U.S. Cl.
CPC ............. *A61B 2034/2048* (2016.02); *A61B 2034/2053* (2016.02); *A61B 2034/2055* (2016.02); *A61B 2090/0818* (2016.02); *A61B 2090/3945* (2016.02); *A61B 2090/3983* (2016.02); *Y10S 901/47* (2013.01)

(58) Field of Classification Search
CPC .... A61B 2034/2053; A61B 2034/2055; A61B 2090/0818; A61B 2090/3945; A61B 2090/3983; Y10S 901/47
See application file for complete search history.

(56) References Cited

U.S. PATENT DOCUMENTS

| | | |
|---|---|---|
| 5,408,409 A | 4/1995 | Glassman et al. |
| 5,494,034 A | 2/1996 | Schlondorff et al. |
| 5,497,061 A | 3/1996 | Nonaka et al. |
| 5,506,682 A | 4/1996 | Pryor |
| 5,569,578 A | 10/1996 | Mushabac |
| 5,577,502 A | 11/1996 | Darrow et al. |
| 5,592,401 A | 1/1997 | Kramer |
| 5,630,431 A | 5/1997 | Taylor |
| 5,638,819 A | 6/1997 | Manwaring et al. |
| 5,662,111 A | 9/1997 | Cosman |
| 5,676,673 A | 10/1997 | Ferre et al. |
| 5,682,886 A | 11/1997 | Delp et al. |
| 5,704,897 A | 1/1998 | Truppe |
| 5,729,475 A | 3/1998 | Romanik, Jr. |
| 5,730,129 A | 3/1998 | Darrow et al. |
| 5,765,561 A | 6/1998 | Chen et al. |
| 5,800,352 A | 9/1998 | Ferre et al. |
| 5,803,089 A | 9/1998 | Ferre et al. |
| 5,828,770 A | 10/1998 | Leis et al. |
| 5,829,444 A | 11/1998 | Ferre et al. |
| 5,848,967 A | 12/1998 | Cosman |
| 5,923,417 A | 7/1999 | Leis |
| 5,930,741 A | 7/1999 | Kramer |
| 5,953,683 A | 9/1999 | Hansen et al. |
| 5,967,980 A | 10/1999 | Ferre et al. |
| 5,976,156 A | 11/1999 | Taylor et al. |
| 6,006,126 A | 12/1999 | Cosman |
| 6,026,315 A | 2/2000 | Lenz et al. |
| 6,061,644 A | 5/2000 | Leis |
| 6,106,464 A | 8/2000 | Bass et al. |
| 6,115,128 A | 9/2000 | Vann |
| 6,122,538 A | 9/2000 | Sliwa, Jr. et al. |
| 6,161,033 A | 12/2000 | Kuhn |
| 6,167,295 A | 12/2000 | Cosman |
| 6,175,756 B1 | 1/2001 | Ferre et al. |
| 6,226,548 B1 | 5/2001 | Foley et al. |
| 6,228,089 B1 | 5/2001 | Wahrburg |
| 6,234,983 B1 | 5/2001 | Storey et al. |
| 6,235,038 B1 | 5/2001 | Hunter et al. |
| 6,236,875 B1 | 5/2001 | Bucholz et al. |
| 6,246,898 B1 | 6/2001 | Vesely et al. |
| 6,266,142 B1 | 7/2001 | Junkins et al. |
| 6,273,896 B1 | 8/2001 | Franck et al. |
| 6,275,725 B1 | 8/2001 | Cosman |
| 6,285,902 B1 | 9/2001 | Kienzle, III et al. |
| 6,288,785 B1 | 9/2001 | Frantz et al. |
| 6,314,312 B1 | 11/2001 | Wessels et al. |
| 6,322,567 B1 | 11/2001 | Mittelstadt et al. |
| 6,341,231 B1 | 1/2002 | Ferre et al. |
| 6,351,659 B1 | 2/2002 | Vilsmeier |
| 6,351,661 B1 | 2/2002 | Cosman |
| 6,400,460 B1 | 6/2002 | Chen |
| 6,409,687 B1 | 6/2002 | Foxlin |
| 6,442,416 B1 | 8/2002 | Schultz |
| 6,442,417 B1 | 8/2002 | Shahidi et al. |
| 6,445,943 B1 | 9/2002 | Ferre et al. |
| 6,450,978 B1 | 9/2002 | Brosseau et al. |
| 6,456,868 B2 | 9/2002 | Saito et al. |
| 6,466,815 B1 | 10/2002 | Saito et al. |
| 6,473,635 B1 | 10/2002 | Rasche |
| 6,490,467 B1 | 12/2002 | Bucholz et al. |
| 6,491,702 B2 | 12/2002 | Heilbrun et al. |
| 6,527,443 B1 | 3/2003 | Vilsmeier et al. |
| 6,581,000 B2 | 6/2003 | Hills et al. |
| 6,584,339 B2 | 6/2003 | Galloway, Jr. et al. |
| 6,584,378 B1 | 6/2003 | Anfindsen |
| 6,585,651 B2 | 7/2003 | Nolte et al. |
| 6,611,141 B1 | 8/2003 | Schulz et al. |
| 6,665,079 B1 | 12/2003 | Tocci et al. |
| 6,675,032 B2 | 1/2004 | Chen et al. |
| 6,675,040 B1 | 1/2004 | Cosman |
| 6,675,122 B1 | 1/2004 | Markendorf et al. |
| 6,691,074 B1 | 2/2004 | Moriya et al. |
| 6,694,167 B1 | 2/2004 | Ferre et al. |
| 6,711,431 B2 | 3/2004 | Sarin et al. |
| 6,757,582 B2 | 6/2004 | Brisson et al. |
| 6,848,304 B2 | 2/2005 | Geen |
| 6,876,926 B2 | 4/2005 | Kirkland et al. |
| 6,926,709 B2 | 8/2005 | Bieger et al. |
| 6,963,409 B2 | 11/2005 | Benner et al. |
| 7,072,704 B2 | 7/2006 | Bucholz |
| 7,104,996 B2 | 9/2006 | Bonutti |
| 7,139,601 B2 | 11/2006 | Bucholz et al. |
| 7,166,114 B2 | 1/2007 | Moctezuma De La Barrera et al. |
| 7,206,627 B2 | 4/2007 | Abovitz et al. |
| 7,209,028 B2 | 4/2007 | Boronkay et al. |
| 7,217,276 B2 | 5/2007 | Henderson et al. |
| 7,283,892 B1 | 10/2007 | Boillot et al. |
| 7,289,227 B2 | 10/2007 | Smetak et al. |
| 7,295,891 B2 | 11/2007 | Huttenhofer et al. |
| 7,395,181 B2 | 7/2008 | Foxlin |
| 7,421,343 B2 | 9/2008 | Hawkinson |
| 7,535,411 B2 | 5/2009 | Falco |
| 7,542,791 B2 | 6/2009 | Mire et al. |
| 7,556,428 B2 | 7/2009 | Sukovic et al. |
| 7,640,106 B1 | 12/2009 | Stokar et al. |
| 7,689,321 B2 | 3/2010 | Karlsson |
| 7,702,379 B2 | 4/2010 | Avinash et al. |
| 7,725,162 B2 | 5/2010 | Malackowski et al. |
| 7,725,279 B2 | 5/2010 | Luinge et al. |
| 7,728,868 B2 | 6/2010 | Razzaque et al. |
| 7,747,312 B2 | 6/2010 | Barrick et al. |
| 7,862,570 B2 | 1/2011 | Russell et al. |
| 7,868,610 B2 | 1/2011 | Velinsky et al. |
| 7,895,761 B2 | 3/2011 | Pettersson |
| 8,010,180 B2 | 8/2011 | Quaid et al. |
| 8,028,580 B2 | 10/2011 | Millet |
| 8,047,075 B2 | 11/2011 | Nasiri et al. |
| 8,057,407 B2 | 11/2011 | Martinelli et al. |
| 8,057,479 B2 | 11/2011 | Stone |
| 8,057,482 B2 | 11/2011 | Stone et al. |
| 8,072,614 B2 | 12/2011 | Deliwala |
| 8,082,064 B2 | 12/2011 | Kay |
| 8,096,163 B2 | 1/2012 | Goldbach |
| 8,100,769 B2 | 1/2012 | Rabin |
| 8,103,472 B2 | 1/2012 | Braun et al. |
| 8,109,890 B2 | 2/2012 | Kamiar et al. |
| 8,111,407 B2 | 2/2012 | Takimasa et al. |
| 8,112,292 B2 | 2/2012 | Simon |
| 8,126,535 B2 | 2/2012 | Maier et al. |
| 8,131,344 B2 | 3/2012 | Strommer et al. |

(56) References Cited

U.S. PATENT DOCUMENTS

| | | | |
|---|---|---|---|
| 8,141,424 B2 | 3/2012 | Seeger et al. | |
| 8,165,844 B2 | 4/2012 | Luinge et al. | |
| 8,849,374 B2 | 9/2014 | Yamamoto et al. | |
| 9,008,757 B2 * | 4/2015 | Wu | A61B 34/20 600/407 |
| 9,271,804 B2 | 3/2016 | Wu | |
| 9,381,085 B2 | 7/2016 | Axelson, Jr. et al. | |
| 9,480,534 B2 | 11/2016 | Bowling et al. | |
| 9,687,307 B2 * | 6/2017 | Wu | A61B 5/064 |
| 9,707,043 B2 | 7/2017 | Bozung | |
| 10,575,906 B2 * | 3/2020 | Wu | A61B 5/064 |
| 2001/0011175 A1 | 8/2001 | Hunter et al. | |
| 2001/0037064 A1 | 11/2001 | Shahidi | |
| 2002/0052546 A1 | 5/2002 | Frantz et al. | |
| 2002/0120192 A1 | 8/2002 | Nolte et al. | |
| 2002/0198448 A1 | 12/2002 | Zuk et al. | |
| 2003/0031349 A1 | 2/2003 | Giorgi et al. | |
| 2003/0163142 A1 | 8/2003 | Paltieli et al. | |
| 2004/0024309 A1 | 2/2004 | Ferre et al. | |
| 2004/0027587 A1 | 2/2004 | Morimoto | |
| 2004/0068178 A1 | 4/2004 | Govari | |
| 2004/0138556 A1 | 7/2004 | Cosman | |
| 2004/0149036 A1 | 8/2004 | Foxlin et al. | |
| 2004/0150560 A1 | 8/2004 | Feng et al. | |
| 2004/0167688 A1 | 8/2004 | Karlsson et al. | |
| 2004/0172164 A1 | 9/2004 | Habibi et al. | |
| 2004/0204646 A1 | 10/2004 | Nagler et al. | |
| 2004/0243148 A1 | 12/2004 | Wasielewski | |
| 2005/0049485 A1 | 3/2005 | Harmon et al. | |
| 2005/0085717 A1 | 4/2005 | Shahidi | |
| 2005/0085718 A1 | 4/2005 | Shahidi | |
| 2005/0154295 A1 | 7/2005 | Quistgaard et al. | |
| 2005/0245820 A1 | 11/2005 | Sarin | |
| 2005/0267353 A1 | 12/2005 | Marquart et al. | |
| 2006/0142657 A1 | 6/2006 | Quaid et al. | |
| 2006/0173356 A1 | 8/2006 | Feilkas | |
| 2006/0178775 A1 | 8/2006 | Zhang et al. | |
| 2006/0190012 A1 | 8/2006 | Freitag | |
| 2006/0258938 A1 | 11/2006 | Hoffman et al. | |
| 2006/0282873 A1 | 12/2006 | Zalewski et al. | |
| 2007/0225731 A1 | 9/2007 | Couture et al. | |
| 2007/0270686 A1 | 11/2007 | Ritter et al. | |
| 2007/0270690 A1 | 11/2007 | Woerlein | |
| 2007/0287911 A1 | 12/2007 | Haid et al. | |
| 2008/0018912 A1 | 1/2008 | Schreiber | |
| 2008/0039868 A1 | 2/2008 | Tuemmler et al. | |
| 2008/0119726 A1 | 5/2008 | Immerz et al. | |
| 2008/0154125 A1 | 6/2008 | Maier et al. | |
| 2008/0161682 A1 | 7/2008 | Kendrick et al. | |
| 2008/0192263 A1 | 8/2008 | Wienand et al. | |
| 2009/0030608 A1 | 1/2009 | Soehren et al. | |
| 2009/0048779 A1 | 2/2009 | Zeng et al. | |
| 2009/0088629 A1 | 4/2009 | Groszmann et al. | |
| 2009/0143670 A1 | 6/2009 | Daigneault | |
| 2009/0149740 A1 | 6/2009 | Hoheisel | |
| 2009/0248044 A1 | 10/2009 | Amiot et al. | |
| 2009/0281417 A1 | 11/2009 | Hartmann et al. | |
| 2009/0312629 A1 | 12/2009 | Razzaque et al. | |
| 2009/0318836 A1 | 12/2009 | Stone et al. | |
| 2010/0030063 A1 | 2/2010 | Lee et al. | |
| 2010/0039506 A1 | 2/2010 | Sarvestani et al. | |
| 2010/0080417 A1 | 4/2010 | Qureshi et al. | |
| 2010/0100081 A1 | 4/2010 | Tuma et al. | |
| 2010/0130853 A1 | 5/2010 | Chandonnet et al. | |
| 2010/0154540 A1 | 6/2010 | Uemura | |
| 2010/0160771 A1 | 6/2010 | Gielen et al. | |
| 2010/0234770 A1 | 9/2010 | Colombet et al. | |
| 2010/0261999 A1 | 10/2010 | Soubelet et al. | |
| 2010/0318223 A1 | 12/2010 | Motoyoshi et al. | |
| 2011/0045736 A1 | 2/2011 | Wooten | |
| 2011/0054304 A1 | 3/2011 | Markowitz et al. | |
| 2011/0087092 A1 | 4/2011 | Kienzle, III | |
| 2011/0105895 A1 | 5/2011 | Kornblau et al. | |
| 2011/0125006 A1 | 5/2011 | Yamamoto et al. | |
| 2011/0178394 A1 | 7/2011 | Fitzpatrick | |
| 2011/0190790 A1 | 8/2011 | Summerer et al. | |
| 2011/0218458 A1 | 9/2011 | Valin et al. | |
| 2011/0257909 A1 | 10/2011 | Allen et al. | |
| 2011/0275957 A1 | 11/2011 | Bhandari | |
| 2011/0320153 A1 | 12/2011 | Lightcap et al. | |
| 2012/0029389 A1 | 2/2012 | Amiot et al. | |
| 2012/0089014 A1 | 4/2012 | Sabczynski et al. | |
| 2012/0095330 A1 | 4/2012 | Shechter et al. | |
| 2012/0108954 A1 | 5/2012 | Schulhauser et al. | |
| 2012/0108955 A1 | 5/2012 | Razzaque et al. | |
| 2012/0165655 A1 | 6/2012 | Mucha | |
| 2013/0064427 A1 | 3/2013 | Picard et al. | |
| 2013/0345718 A1 | 12/2013 | Crawford et al. | |
| 2018/0333214 A1 | 11/2018 | Han et al. | |

FOREIGN PATENT DOCUMENTS

| | | |
|---|---|---|
| CN | 102449666 A | 5/2012 |
| DE | 4225112 C1 | 12/1993 |
| DE | 102004047905 A1 | 4/2006 |
| DE | 102004061764 A1 | 7/2006 |
| JP | 2008538184 A | 10/2008 |
| JP | 2009254805 A | 11/2009 |
| WO | 199611624 A2 | 4/1996 |
| WO | 200200131 A1 | 1/2002 |
| WO | 2006091494 A1 | 8/2006 |
| WO | 2008100472 A2 | 8/2008 |
| WO | 2010077008 A2 | 7/2010 |
| WO | 2010086374 A1 | 8/2010 |
| WO | 2010096419 A2 | 8/2010 |
| WO | 2010111090 A1 | 9/2010 |
| WO | 2010150148 A1 | 12/2010 |
| WO | 2011025708 A2 | 3/2011 |
| WO | 2011026077 A2 | 3/2011 |
| WO | 2011059383 A1 | 5/2011 |
| WO | 2011089606 A1 | 7/2011 |
| WO | 2011106861 A1 | 9/2011 |
| WO | 2011128766 A2 | 10/2011 |
| WO | 2011133927 A2 | 10/2011 |
| WO | 2011128766 A3 | 12/2011 |
| WO | 2012052070 A1 | 4/2012 |
| WO | 2012080840 | 6/2012 |

OTHER PUBLICATIONS

A Novel Approach to Computer Assisted Spine Surgery, Lutz P. Nolte, Lucia J. Zamorano, Zhaowel Jlang, Qinghai Wang, Frank Langlotz, Erich Arm, Heiko Visarius, Proceedings of the First International Symposium on Medical Robotics and Computer AssistedSurgery, vol. 2, Workshop [Part I & II] Session VI, Sep. 1994, pp. 323-328, 7 pages.

A review of robotics in surgery, B. Davies, Proceedings of the Institution of Mechanical Engineers Part H: Journal of Engineering in Medicine, 2000, pp. 129-140, 13 pages.

A Robotized Surgeon Assistant, T. Wang, M. Fadda, M. Marcacci, S. Martelli, P. Dario and A. Visani, Intelligent Robots and Systems '94. 'Advanced Robotic Systems and the Real World', IROS '94. Proceedings of the IEEE/RSJ/GI International Conferenceon (vol. 2) pp. 852-868, 1994, 8 pages.

A Safe Robot System for Craniofacial Surgery, D. Engel, J. Raczkowsky, H. Worn, May 21-26, 2001, Proceedings of the 2001 IEEE, International Conference on Robotics and Automation, pp. 2020-2024, 5 pages.

A Steady-Hand Robotic System for Microsurgical Augmentation, Russell Taylor, Pat Jensen, Louis Whitcomb, Aaron Barnes, Rajest Kumar, Dan Stoianovici, Puneet Gupta, Zhengxian Wange, Eugen Dejuan and Louis Kavoussi, The International Journal ofRobotics Research, 1999, vol. 18, pp. 1201-1210, 11 pages.

A Stereotactic/Robotic System for Pedicle Screw Placement, Julio J. Santos-Munne, Michael A. Peshkin, Srdjan Mirkovic, S. David Stulberg, Thomas C. Kienzle III, 1995, Interactive Technology and the New Paradigm for Hardware, pp. 326-333, 8 pages.

Accuracy Study on the Registration of the Tibia by Means of an Intramedullary Rod in Robot-Assisted Total Knee Arthroplasty, G. Van Ham, J. Bellemans, K. Denis, L. Labey, J. Vander Sloten, R.

(56) References Cited

OTHER PUBLICATIONS

Van Audekercke, G. Van Der Perre, J. De Schutter, 46thAnnual Meeting, Orthopaedic Research Society, Mar. 2000, pp. 450, 1 page.
Accuracy Validation in Image-Guided Orthopaedic Surgery, David Simon, R.V. O'Toole, Mike Blackwell, F. Morgan, Anthony M. Digioia, and Takeo Kanade, Proceedings of the Second International Symposium on Medical Robotics and Computer Assisted Surgery,1995, pp. 185-192, 8 pages.
Acrobot—Using Robots and Surgeons Synergistically in Knee Surgery, BL Davies, KL Fan, RD Hibberd, M. Jakopec and SJ Harris, Mechatronics in Medicine, Jul. 1997, pp. 173-178, 6 pages.
Active compliance in robotic surgery—the use of force control as a dynamic constraint, B.L. Davies, S. J. Harris, W. J. Lin, R. D. Hibberd, R. Middleton and J.C. Cobb, Proceedings of the Institution of Mechanical Engineers, Part H: Journal ofEngineering in Medicine, 1997 vol. 211, pp. 285-292; 9 pages.
An Image-directed Robotic System for Hip Replacement Surgery, Russell H. Taylor, Howard A. Paul, Brent D. Mittelstadt, William Hanson, Peter Kazanzides, Joel Zuhars, Edward Glassman, Bela L. Musits, Bill Williamson, William L. Bargar, Oct. 1990, pp. 111-118, 7 pages.
An Integrated CAD-Robotics System for Total Knee Replacement Surgery, Kienzle, T.C., III, 1993, IEEE, pp. 889-894, 6 pages.
Architecture of a Surgical Robot, P. Kazanzides, J. Zuhars, B. Mittelstadt, B. Williams, P. Cain, F. Smith, L. Rose, B. Musits, 1992 IEEE, pp. 1624-1629, 6 pages.
Clinical Introduction of the Caspar System Problems and Initial Results, C.O.R. Grueneis, R.H. Richter, F.F. Hennig, Abstracts from CAOS, 1999, pp. 160, 1 page.
Comparative Tracking Error Analysis of Five Different Optical Tracking Systems, R Khadem, C C Yeh, M Sadeghi-Tehrani, M R Bax, J A Johnson, J N Welch, E P Wilkinson, R Shahidi, Computer Aided Surgery vol. 5, 2000, pp. 98-107.
Comparison of Relative Accuracy Between a Mechanical and an Optical Position Tracker for Image-Guided Neurosurgery, Rohling R, Munger P, Hollerbach JM, Peter T., J Image Guid Surg., 1995;1(1), pp. 30-34, 4 pages.
Computer Assisted Knee Replacement, Scott L. Delp, Ph.D., S. David Stulberg, MD, Brian Davies, Ph.D. Frederic Picard, MD and Francois Leitner, Ph.D., Clinical Orthopaedics, Sep. 1998, vol. 354, pp. 49-56; 8 pages.
Computer Assisted Orthopaedic Surgery Image Guided and Robotic Assistive Technologies, Anthony M. Digioia, Branislav Jaramaz, and B. Colgan, Clinical Orthopaedics and Related Research, No. 354, Sep. 1998, pp. 8-16, 9 pages.
Computer Assisted Planning for Total Knee Arthroplasty, CVRMed-MRCAS'97, M. Fadda, D. Bertelli, S. Martelli, M. Marcacci, P. Dario, C. Paggetti, D. Caramella, D. Tripp!, 1997, pp. 619-628, 10 pages.
Computer Assisted Spine Surgery: a technique for accurate transpedicular screw fixation, S Lavallee, Proceedings of the First International Symposium on Medical Robotics and Computer Assisted Surgery, vol. 2, Workshop [Part I & II] Session VI, Sep. 1994, pp. 315-322, 9 pages.
Computer-assisted and robotics surgery, Brian Davies, International Congress and Symposium Series 223, 1997, pp. 71-82; 12 pages.
Computer-Assisted Knee Arthroplasty at Rizzoli Institutes, M. Fadda, Proceedings of the First International Symposium on Medical Robotics and Computer Assisted Surgery, Sep. 1994, pp. 26-30, 6 pages.
Concepts and methods of registration for computer-integrated surgery, E. Bainville, I. Bricault, P. Cinquin, and S. Lavallee, Computer Assisted Orthopedic Surgery ("CAOS"), L.-P. Nolte and R. Ganz, Eds., pp. 15-34, Hogrefe & Huber, Seattle, Wash,USA, 1999; 22 pages.
Crigos A Compact Robot for Image-Guided Orthopedic Surgery, Guido Brandt, Andreas Zimolong, Lional Carrat, Philippe Merloz, Hans-Walter Staudte, Stephane Lavallee, Klaus Rademacher and Gunter Rau, Dec. 1999, IEEE Transactions on InformationTechnology in Biomedicine, vol. 3, No. 4, pp. 252-260, 9 pages.

Design Optically Tracked Instruments for Image Guided Surgery, Jay B. West and Calvin R. Maurer, Jr., Member, IEEE Transactions on Medical Imaging, vol. 23, No. 5, May 2004, 13 pages.
Digital surgery the future of medicine and human-robot symbiotic interaction, Rony A. Abovitz, Industrial Robot: An International Journal, vol. 28, No. 5, 2001, pp. 401-405, 5 pages.
EasyGuide Neuro, ein neues System zur bildgefuhrten Planung, Simulation und Navigation in der Neurochirurgie, TH. Schmidt und W. Hentschel, 1995, Biomedizinische Technik, Band 40, Erganzungsband 1, pp. 233-234; 2 pages.
Ein Robotersystem fur craniomaxillofaciale chirurgische Eingriffe, J. Raczkowsky, J. Munchenberg, I. Bertovic, C. Burghart, Informatik Forsch. Entw., 1999, pp. 24-35, 12 pages.
English language abstract and machine-assisted English translation for CN 202146362 extracted from espacenet.com database on Sep. 28, 2017, 10 pages.
English language abstract and machine-assisted English translation for DE 4225112 extracted from espacenet.com database on Sep. 28, 2017, 12 pages.
English language abstract for CN 102449666 extracted from espacenet.com database on Sep. 28, 2017, 2 pages.
English language abstract for JP 2008-538184 extracted from espacenet.com database on Apr. 29, 2019, 2 pages.
English language abstract for JP 2009-254805 extracted from espacenet.com database on Mar. 20, 2019, 2 pages.
Experiences with Robotic Systems for Knee Surgery, S. J. Harris, W. J. Lin, K. L. Fan, R. D. Hibberd, J. Cobb, R. Middleton, B. L. Davies, CVRMed-MRCAS'97, Lecture Notes in Computer Science vol. 1205, 1997, pp. 757-766; 10 pages.
Force Control for Robotic Surgery, S.C. Ho, R.D. Hibberd, J. Cobb and B.L. Davies, ICAR, 1995, pp. 21-32, 12 pages.
Frameless Neuronavigation in Modern Neurosurgery, Spetzger U, Laborde G, Gilsbach JM, Minim. Invas, Neurosurg., 1995, vol. 38, pp. 163-166, 4 pages.
G.C. Claasen, P. Martin, F. Picard, Tracking and Control for Handheld Surgery Tools, Biomedical Circuits and Systems Conference (BioCAS), 2011 IEEE, pp. 428-431, IEEE, San Diego, CA, USA; 4 pages.
Haptic information displays for computer-assisted surgery, A.E. Quaid and Rony A. Abovitz, Robotics and Automation, 2002 Proceedings ICRA '02. IEEE International Conference on Robotics and Automation, 2092, vol. 2, pp. 2092-2097, 6 pages.
High-Bandwidth Low-Latency Tracking Using Optical and Inertial Sensors, Gontje C. Claasen and Philippe Martin, Centre Automatique et Systemes, and Frederic Picard, Department of Ofthopaedics, Golden Jubilee National Hospital, Proceedings of the 5thInternational Conference on Automation, Robotics and Applications, Dec. 6-8, 2011, Wellington, New Zealand, 6 pages.
Human-Interactive Medical Robotics, Rony A. Abovitz, M.S., Computer Assisted Orthopedic Surgery ("CAOS"), 2000, pp. 71-72, 2 pages.
Image-Guided Manipulator Compliant Surgical Planning Methodology for Robotic Skull-Base Surgery, Wan Sing Ng; Ming Yeong Teo; Yong-Chong Loh; Tseng Tsai Yeo, Medical Imaging and Augmented Reality, 2001 IEEE, pp. 26-29, 4 pages.
Inertial and Magnetic Sensing of Human Motion, Daniel Roetenberg, May 24, 2006, 128 pages.
International Search Report of the International Searching Authority for Application No. PCT/US2013/061642 dated Jan. 20, 2014; 7 pages.
Intra-operative Application of a Robotic Knee Surgery System, S. J. Harris, M. Jakopec, J. Cobb, B. L. Davies, Medical Image Computing and Computer-Assisted Intervention—MICCAI'99, Lecture Notes in Computer Science vol. 1679, 1999, pp. 1116-1124; 9pages.
Intraoperative Navigation Techniques Accuracy Tests and Clinical Report, S. Hassfeld, C. Burghart, I. Bertovic, J. Raczkowsky, U. Rembod, H. Worn and J. Muling, 1998, pp. 670-675, 6 pages.
Machining and Accuracy Studies for a Tibial Knee Implant Using a Force-Controlled Robot, Computer Aided Surgery, 1998, pp. 123-133, 11 pages.

(56) References Cited

OTHER PUBLICATIONS

Minimally Invasive Total Knee Arthroplasty Surgery Through Navigated Freehand Bone Cutting, Hani Haider, PHD, O. Andres Barrera, MSC, and Kevin L. Garvin, MD, The Journal of Arthroplasty, vol. 22, No. 4, 2007, 8 pages.
Precision Freehand Sculpting of Bone, Gabriel Brisson, Takeo Kanade, Anthony Digioia, Branislav Jaramaz, MICCAI 2004, LNCS 3217, pp. 105-112, 2004, 8 pages.
PrecisioN Knee Navigation Operative Technique, Stryker Software Manual, Knute Buehler, M.D., Chief of Arthritis and Joint Reconstruction the Center—Orthopedic and Neurosurgery Care and Research Bend, Oregon 40 pages.
Premiers Pas Vers La Dissectomie et la Realisation de Protheses du Genou a L'Aide de Robots, M. Fadda, S. Martelli, P. Dario, M. Marcacci, S. Zaffagnini, A. Visani, Innov. Tech. Biol. Med., vol. 13, No. 4, 1992, pp. 394-409, 16 pages.
Primary and Revision Total Hip Replacement Using the Robodoc System, William L. Bargar, MD, Andre Bauer, MD and Martin Borner, MD, Clinical Orthopaedics and Related Research, 1998, No. 354, pp. 82-91, 10 pages.
Registration and immobilization in robot-assisted surgery, Jon T. Lea, Dane Watkins, Aaron Mills, Michael A. Peshkin, Thomas C. Kienzle III and S. David Stulberg, Journal of Image Guided Surgery, 1995, vol. 1, No. 2, pp. 80-87, 11 pages.
Registration Graphs a Language for Modeling and Analyzing Registration in Image-Guided Surgery, Jon Thomas Lea, Dec. 1998, 1-49, 49 pages.
Robot assisted craniofacial surgery: first clinical evaluation, C. Burghart, R. Krempien, T. Redlich, A. Pernozzoli, H. Grabowski, J. Muenchenberg, J. Albers, S. Ha.beta.eld, C. Vahl, U. Rembold and H. Woern, 1999, 7 pages.
Robot Assisted Knee Surgery, 4527 IEEE, Engineering in Medicine & Biology 14, May/Jun. 1995, No. 3, pp. 292-300, 9 pages.
Robot Controlled Osteotomy in Craniofacial Surgery, Catherina Burghart, Jochen Keitel, Stefan Hassfeld, Ulrich Rembold and Heinz Woern, Haptic Devices in Medical Applications, Jun. 23, 1999; pp. 12-22, 13 pages.
Robotergestutzte Osteotomie in der craniofacialen Chirurgie, Catherina R. Burghart, GCA-Verlag, 2000, and partial English translation, 250 pages.
Robotic Assistance in Orthopaedic Surgery A Proof of Principle Using Distal Femoral Arthroplasty, Clinical Orthopaedics and Related Research, 1993, No. 296, pp. 178-186, 9 pages.
Robotic Execution of a Surgical Plan, Howard A. Paul, DVM, William L. Bargar, MD, Brent Mittlestadt, Peter Kazanzides, PH.D., Bela Musites, Joel Suhars, Phillip W. Cain, Bill Williamson, Fred G. Smith, 1992 IEEE, 99. 1621-1623, 3 pages.
Robotics in Minimally Invasive Surgery, Brian Davies, Mechatronics in Medicine Lab, IEE, 1996 The Institution of Electrical Engineers, pp. 1-2, 2 pages.
Robotics in surgery a new generation of surgical tools incorporate computer technology and mechanical actuation to give surgeons much finer control than previously possible during some operations, Rob Buckingham, IEE Review, Sep. 1994, pp. 193-196,4 pages.
Robust Multi Sensor Pose Estimation for Medical Applications, Andreas Tobergte, Mihai Pomarlan and Gerd Hirzinger, 8 pages.
Safe Active Robotic Devices for Surgery, Ro Buckingham, Oct. 1993, vol. 5, pp. 355-358, 4 pages.

Section 4 Robotic Systems and Task-Level Programming, A Model-Based Optimal Planning and Execution System with Active Sensing and Passive Manipulation for Augmentation of Human Precision in Computer-Integrated Surgery, Russell H. Taylor, Yong-YilKim, Alan D. Kalvin, David Larose, Betsy Haddad, Deljou Khoramabadi, Marilyn Noz, Robert Olyha, Nils Brunn and Dieter Grimm, Experimental Robotics II Lecture Notes in Control and Information Sciences, vol. 190, 1993, pp. 177-195, 19 pages.
Semi-Active Guiding Systems in Surgery. A Two-DOF Prototype of the Passive Arm with Dynamic Constraints (PADyC), Jocelyne Troccaz, Yves Delnondedieu, Mechatronics vol. 6, No. 4, pp. 399-421, 1996, 23 pages.
Surgical Robot for Total Hip Replacement Surgery, Proceedings of the 1992 IEEE, International Conference on Robotics and Automation, May, 1992, pp. 606-611, 6 pages.
Surgical Robotics an Introduction, Ulrich Rembold and Catherina R. Burghart, Journal of Intelligent and Robotic Systems, vol. 30, Institute of Process Control and Robotics, 2001, pp. 1-28, 28 pages.
Technique and first clinical results of robot-assisted total knee replacement, Werner Siebert, Sabine Mai, Rudolf Kober and Peter F. Heeckt, The Knee, vol. 9, 2002, pp. 173-130, 8 pages.
The Robodoc Clinical Trial A Robotic Assistant for Total Hip Arthroplasty, Evelyn Harkins Spencer, Orthopaedic Nursing, Jan./Feb. 1996, vol. 15, No. 1, pp. 9-14, 6 pages.
Three-Dimensional Digitizer (Neuronavigator); New Equipment for Computed Tomography-Guided Stereotaxic Surgery, Watanabe E, Watanabe T, Manaka S, Mayanagi Y, Takakura K., Surg Neurol., Jun. 1987, Issue 6, pp. 543-547, 5 pages.
Three-Dimensional Ultrasound Imaging Using Multiple Magnetic Tracking Systems and Miniature Sensors, Daniel F. Leotta, Paul R. Detmer, Odd Helge Gilja, Jing-Ming Jong, Roy W. Martin, Jean F. Primozich, Kirk W. Beach and D. Eugene Strandness,Bioengineering, Surgery, Anesthesiology, University of Washington, Seattle, WA, 1995 IEEE Ultrasonics Symposium, 4 pages.
Total Knee Replacement Computer-assisted surgical system uses a calibrated robot, May/Jun. 1995, IEEE Engineering in Medicine and Biology; A Computer-Assisted Total Knee Replacement Surgical System Using a Calibrated Robot, Thomas C. Kienzle III, S.David Stulberg, Michael Peshkin, Arthur Quaid, Jon Lea, Ambarish Goswami, Chi-hau Engineering in Medicine and Biology vol. 14, Issue 3, May 1995, pp. 301-306, 35 pages.
U.S. Appl. No. 61/662,070, filed Jun. 20, 2012.
U.S. Appl. No. 61/679,258, filed Aug. 3, 2012.
Written Opinion of the International Searching Authority for Application No. PCT/US2013/061642 dated Jan. 20, 2014; 7 pages.
A Novel Approach to Computer Assisted Spine Surgery, Lutz P. Nolte, Lucia J. Zamorano, Zhaowel Jiang, Qinghai Wang, Frank Langlotz, Erich Arm, Heiko Visarius, Proceedings of the First International Symposium on Medical Robotics and ComputerAssistedSurgery, vol. 2, Workshop [Part I & II] Session VI, Sep. 1994, pp. 323-328, 7 pages.
G.C. Claasen, P. Martin, F. Picard, Tracking and Control for Handheld Surgery Tools, Biomedical Circuits and System Conference (BioCAS), 2011 IEEE, pp. 428-431, IEEE, San Diego, CA, USA; 4 pages.
English language abstract and machine-assisted English translation for CN 10126776 extracted from espacenet.com database on Jan. 13, 2021, 45 pages.

\* cited by examiner

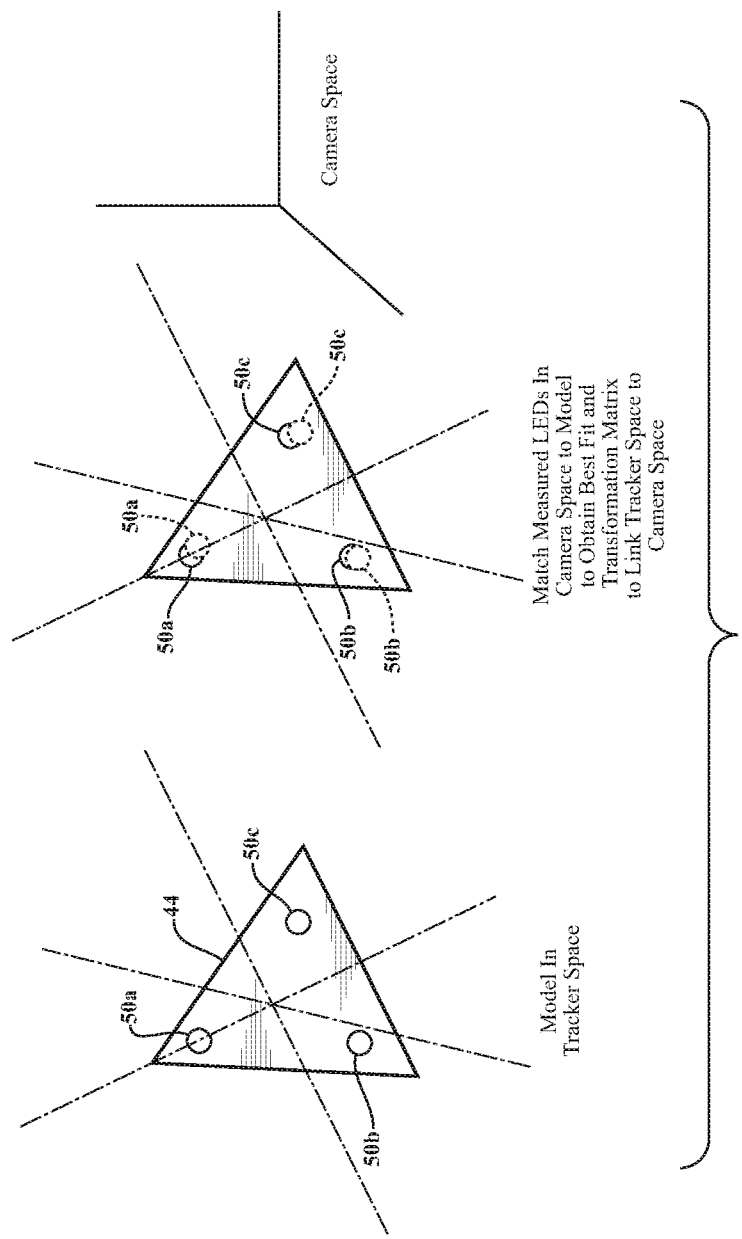

OPTICAL AND NON-OPTICAL SENSOR TRACKING OF OBJECTS FOR A ROBOTIC CUTTING SYSTEM

CROSS-REFERENCE TO RELATED APPLICATIONS

This application is a continuation of U.S. patent application Ser. No. 15/599,935, filed on May 19, 2017, which is a continuation of U.S. patent application Ser. No. 14/994,236, filed on Jan. 13, 2016, which is a continuation of U.S. patent application Ser. No. 14/635,402, filed on Mar. 2, 2015, which is a continuation of U.S. patent application Ser. No. 14/035,207, filed on Sep. 24, 2013, which claims priority to and the benefit of U.S. Provisional Patent Application No. 61/705,804, filed on Sep. 26, 2012, the entire contents of all of which are hereby incorporated by reference.

TECHNICAL FIELD

The present disclosure relates generally to navigation systems and methods that tracks objects in space by determining changes in the position and/or orientation of such objects over time. More specifically, the present disclosure relates to navigation systems and methods that utilize optical sensors and non-optical sensors to determine the position and/or orientation of objects.

BACKGROUND OF THE INVENTION

Navigation systems assist users in precisely locating objects. For instance, navigation systems are used in industrial, aerospace, defense, and medical applications. In the medical field, navigation systems assist surgeons in precisely placing surgical instruments relative to a patient's anatomy.

Surgeries in which navigation systems are used include neurosurgery and orthopedic surgery. Often the instrument and the anatomy are tracked together with their relative movement shown on a display. The navigation system may display the instrument moving in conjunction with a preoperative image or an intraoperative image of the anatomy. Preoperative images are typically prepared by MRI or CT scans, while intraoperative images may be prepared using a fluoroscope, low level x-ray or any similar device. Alternatively, some systems are imageless in which the patient's anatomy is "painted" by a navigation probe and mathematically fitted to an anatomical model for display.

Navigation systems may employ light signals, sound waves, magnetic fields, RF signals, etc. in order to track the position and/or orientation of the instrument and anatomy. Optical navigation systems are widely used due to the accuracy of such systems.

Prior art optical navigation systems typically include one or more camera units that house one or more optical sensors (such as charge coupled devices or CCDs). The optical sensors detect light emitted from trackers attached to the instrument and the anatomy. Each tracker has a plurality of optical emitters such as light emitting diodes (LEDs) that periodically transmit light to the sensors to determine the position of the LEDs.

The positions of the LEDs on the instrument tracker correlate to the coordinates of a working end of the instrument relative to a camera coordinate system. The positions of the LEDs on the anatomy tracker(s) correlate to the coordinates of a target area of the anatomy in three-dimensional space relative to the camera coordinate system. Thus, the position and/or orientation of the working end of the instrument relative to the target area of the anatomy can be tracked and displayed.

Navigation systems can be used in a closed loop manner to control movement of surgical instruments. In these navigation systems both the instrument and the anatomy being treated are outfitted with trackers such that the navigation system can track their position and orientation. Information from the navigation system is then fed to a control system to control or guide movement of the instrument. In some cases, the instrument is held by a robot and the information is sent from the navigation system to a control system of the robot.

In order for the control system to quickly account for relative motion between the instrument and the anatomy being treated, the accuracy and speed of the navigation system must meet the desired tolerances of the procedure. For instance, tolerances associated with cementless knee implants may be very small to ensure adequate fit and function of the implant. Accordingly, the accuracy and speed of the navigation system may need to be greater than in more rough cutting procedures.

One of the limitations on accuracy and speed of optical navigation systems is that the system relies on the line-of-sight between the LEDs and the optical sensors of the camera unit. When the line-of-sight is broken, the system may not accurately determine the position and/or orientation of the instrument and anatomy being tracked. As a result, surgeries can encounter many starts and stops. For instance, during control of robotically assisted cutting, when the line-of-sight is broken, the cutting tool must be disabled until the line-of-sight is regained. This can cause significant delays and added cost to the procedure.

Another limitation on accuracy occurs when using active LEDs on the trackers. In such systems, the LEDs are often fired in sequence. In this case only the position of the actively fired LED is measured and known by the system, while the positions of the remaining, unmeasured LEDs are unknown. In these systems, the positions of the remaining, unmeasured LEDs are approximated. Approximations are usually based on linear velocity data extrapolated from the last known measured positions of the currently unmeasured LEDs. However, because the LEDs are fired in sequence, there can be a considerable lag between measurements of any one LED. This lag is increased with each additional tracker used in the system. Furthermore, this approximation does not take into account rotations of the trackers, resulting in further possible errors in position data for the trackers.

As a result, there is a need in the art for an optical navigation system that utilizes additional non-optically based data to improve tracking and provide a level of accuracy and speed with which to determine position and/or orientations of objects for precise surgical procedures such as robotically assisted surgical cutting.

SUMMARY

In one example, a surgical system is provided that comprises a robotic device, a control system, a first tracker, a second tracker, and a navigation system. The robotic device is configured to support a cutting tool and configured to move the cutting tool in at least three degrees of freedom. The control system is configured to command the robotic device to control or constrain movement of the cutting tool. The first tracker is configured to be coupled to the robotic device. The second tracker is configured to be coupled to an anatomy. The second tracker includes three markers that are configured to generate optical signals. The second tracker also includes a non-optical sensor that is configured to generate non-optical signals. The navigation system is in communication with the control system and includes at least one optical sensor. The navigation system is configured to receive, with the optical sensor, the optical signals from one or more of the three markers. The navigation system is also configured to receive the non-optical signals from the non-optical sensor. The navigation system is also configured to, based on the received optical and non-optical signals, communicate position data indicative of a position of the anatomy to the control system to control the robotic device for cutting of the anatomy.

In one example, a method of operating a surgical system is provided wherein the surgical system comprises a robotic device configured to support a cutting tool and to move the cutting tool in at least three degrees of freedom, a control system configured to command the robotic device to control or constrain movement of the cutting tool, a first tracker configured to be coupled to the robotic device, a second tracker configured to be coupled to an anatomy and the second tracker including three markers configured to generate optical signals and a non-optical sensor configured to generate non-optical signals, and a navigation system in communication with the control system and including at least one optical sensor. The method comprises: receiving, with the optical sensor of the navigation system, the optical signals from one or more of the three markers; receiving, with the navigation system, the non-optical signals from the non-optical sensor; and based on the received optical and non-optical signals, communicating, with the navigation system, position data indicative of a position of the anatomy to the control system to control the robotic device for cutting of the anatomy.

In one example, a navigation system is adapted for a robotic device configured to support a cutting tool and to move the cutting tool in at least three degrees of freedom. The navigation system is in communication with a control system configured to command the robotic device to control or constrain movement of the cutting tool. The navigation system comprises: at least one optical sensor; a first tracker configured to be coupled to the robotic device; a second tracker configured to be coupled to an anatomy and the second tracker including three markers configured to generate optical signals and a non-optical sensor configured to generate non-optical signals; and a computing system including at least one processor configured to: receive, with the optical sensor, the optical signals from one or more of the three markers; receive the non-optical signals from the non-optical sensor; and based on the received optical and non-optical signals, communicate position data indicative of a position of the anatomy to the control system to enable the control system to control the robotic device for cutting of the anatomy.

BRIEF DESCRIPTION OF THE DRAWINGS

Advantages of the present invention will be readily appreciated as the same becomes better understood by reference to the following detailed description when considered in connection with the accompanying drawings wherein:

FIG. 4A is a schematic illustration of matching measured LEDs with a tracker model to obtain a transformation matrix;

DETAILED DESCRIPTION

I. Overview

Figure 1:
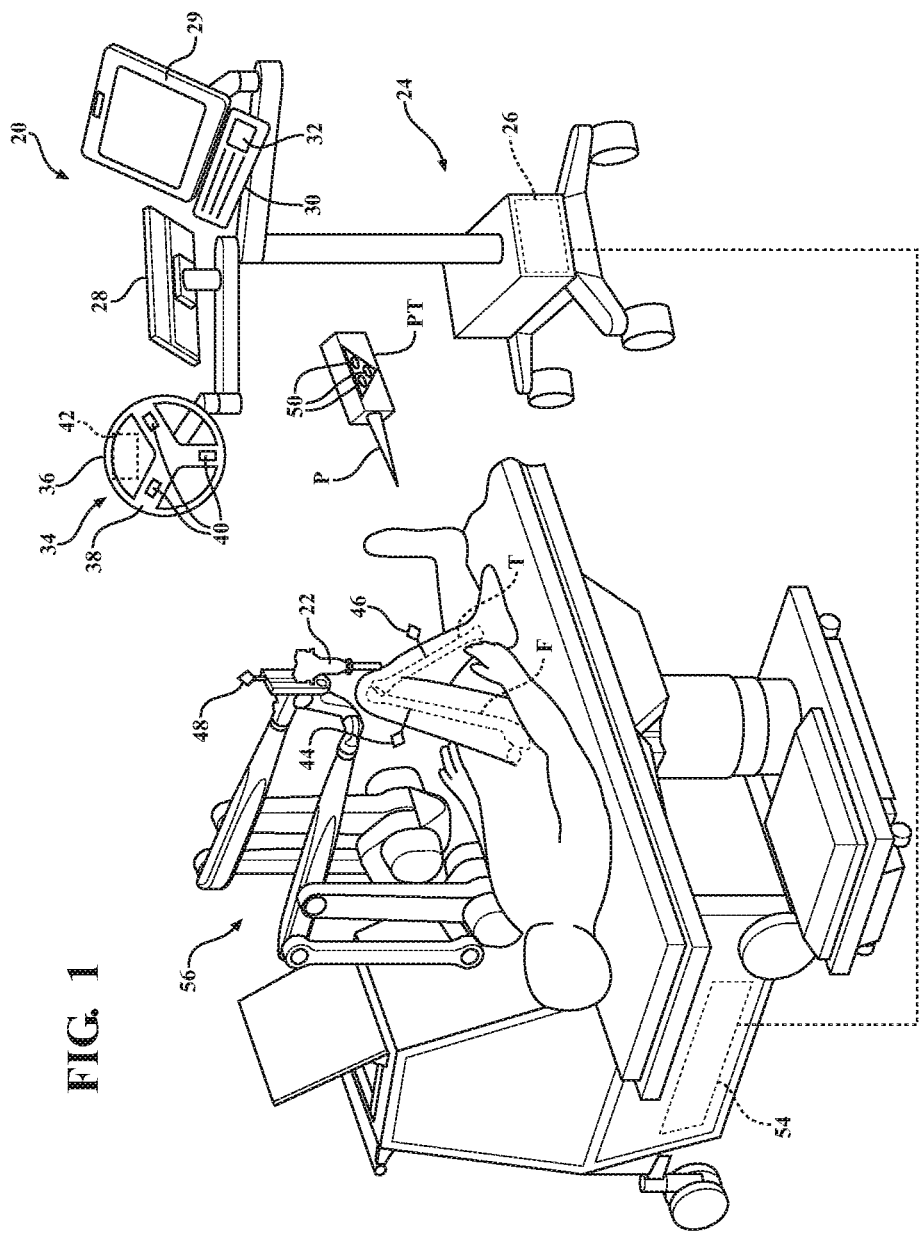
FIG. 1 is a perspective view of a navigation system of the present invention being used in conjunction with a robotic manipulator.

Referring to FIG. 1 a surgical navigation system 20 is illustrated. System 20 is shown in a surgical setting such as an operating room of a medical facility. The navigation system 20 is set up to track movement of various objects in the operating room. Such objects include, for example, a surgical instrument 22, a femur F of a patient, and a tibia T of the patient. The navigation system 20 tracks these objects for purposes of displaying their relative positions and orientations to the surgeon and, in some cases, for purposes of controlling or constraining movement of the surgical instrument 22 relative to a predefined path or anatomical boundary.

The surgical navigation system 20 includes a computer cart assembly 24 that houses a navigation computer 26. A navigation interface is in operative communication with the navigation computer 26. The navigation interface includes a display 28 adapted to be situated outside of the sterile field and a display 29 adapted to be situated inside the sterile field. The displays 28, 29 are adjustably mounted to the computer cart assembly 24. Input devices 30, 32 such as a mouse and keyboard can be used to input information into the navigation computer 26 or otherwise select/control certain aspects of the navigation computer 26. Other input devices are contemplated including a touch screen (not shown) on displays 28, 29 or voice-activation.

A localizer 34 communicates with the navigation computer 26. In the embodiment shown, the localizer 34 is an optical localizer and includes a camera unit 36. The camera unit 36 has an outer casing 38 that houses one or more optical sensors 40. In some embodiments at least two optical sensors 40 are employed, preferably three. The optical sensors 40 may be three separate high resolution charge-coupled devices (CCD). In one embodiment three, one-dimensional CCDs are employed. It should be appreciated that in other embodiments, separate camera units, each with a separate CCD, or two or more CCDs, could also be arranged around the operating room. The CCDs detect infrared (IR) signals.

Camera unit 36 is mounted on an adjustable arm to position the optical sensors 40 above the zone in which the procedure is to take place to provide the camera unit 36 with a field of view of the below discussed trackers that, ideally, is free from obstructions.

The camera unit 36 includes a camera controller 42 in communication with the optical sensors 40 to receive signals from the optical sensors 40. The camera controller 42 communicates with the navigation computer 26 through either a wired or wireless connection (not shown). One such connection may be an IEEE 1394 interface, which is a serial bus interface standard for high-speed communications and isochronous real-time data transfer. Connection could also use a company specific protocol. In other embodiments, the optical sensors 40 communicate directly with the navigation computer 26.

Position and orientation signals and/or data are transmitted to the navigation computer 26 for purposes of tracking the objects. The computer cart assembly 24, display 28, and camera unit 36 may be like those described in U.S. Pat. No. 7,725,162 to Malackowski, et al. issued on May 25, 2010, entitled "Surgery System", hereby incorporated by reference.

The navigation computer 26 can be a personal computer or laptop computer. Navigation computer 26 has the display 28, central processing unit (CPU) and/or other processors, memory (not shown), and storage (not shown). The navigation computer 26 is loaded with software as described below. The software converts the signals received from the camera unit 36 into data representative of the position and orientation of the objects being tracked.

Navigation system 20 includes a plurality of tracking devices 44, 46, 48, also referred to herein as trackers. In the illustrated embodiment, one tracker 44 is firmly affixed to the femur F of the patient and another tracker 46 is firmly affixed to the tibia T of the patient. Trackers 44, 46 are firmly affixed to sections of bone. Trackers 44, 46 may be attached to the femur F in the manner shown in U.S. Pat. No. 7,725,162, hereby incorporated by reference. In further embodiments, an additional tracker (not shown) is attached to the patella to track a position and orientation of the patella. In further embodiments, the trackers 44, 46 could be mounted to other tissue types or parts of the anatomy.

An instrument tracker 48 is firmly attached to the surgical instrument 22. The instrument tracker 48 may be integrated into the surgical instrument 22 during manufacture or may be separately mounted to the surgical instrument 22 in preparation for the surgical procedures. The working end of the surgical instrument 22, which is being tracked, may be a rotating bur, electrical ablation device, or the like. In the embodiment shown, the surgical instrument 22 is an end effector of a surgical manipulator. Such an arrangement is shown in U.S. Provisional Patent Application No. 61/679,258, entitled, "Surgical Manipulator Capable of Controlling a Surgical Instrument in either a Semi-Autonomous Mode or a Manual, Boundary Constrained Mode", the disclosure of which is hereby incorporated by reference, and also in U.S. patent application Ser. No. 13/958,834, entitled, "Navigation System for use with a Surgical Manipulator Operable in Manual or Semi-Autonomous Mode", the disclosure of which is hereby incorporated by reference.

The trackers 44, 46, 48 can be battery powered with an internal battery or may have leads to receive power through the navigation computer 26, which, like the camera unit 36, preferably receives external power.

In other embodiments, the surgical instrument 22 may be manually positioned by only the hand of the user, without the aid of any cutting guide, jib, or other constraining mechanism such as a manipulator or robot. Such a surgical instrument is described in U.S. Provisional Patent Application No. 61/662,070, entitled, "Surgical Instrument Including Housing, a Cutting Accessory that Extends from the Housing and Actuators that Establish the Position of the Cutting Accessory Relative to the Housing", hereby incorporated by reference, and also in U.S. patent application Ser. No. 13/600,888, entitled "Surgical Instrument Including Housing, a Cutting Accessory that Extends from the Housing and Actuators that Establish the Position of the Cutting Accessory Relative to the Housing", hereby incorporated by reference.

The optical sensors 40 of the localizer 34 receive light signals from the trackers 44, 46, 48. In the illustrated embodiment, the trackers 44, 46, 48 are active trackers. In this embodiment, each tracker 44, 46, 48 has at least three active markers 50 for transmitting light signals to the optical sensors 40. The active markers 50 can be light emitting diodes or LEDs 50. The optical sensors 40 preferably have sampling rates of 100 Hz or more, more preferably 300 Hz or more, and most preferably 500 Hz or more. In some embodiments, the optical sensors 40 have sampling rates of 1000 Hz. The sampling rate is the rate at which the optical sensors 40 receive light signals from sequentially fired LEDs 50. In some embodiments, the light signals from the LEDs 50 are fired at different rates for each tracker 44, 46, 48.

Figure 2:
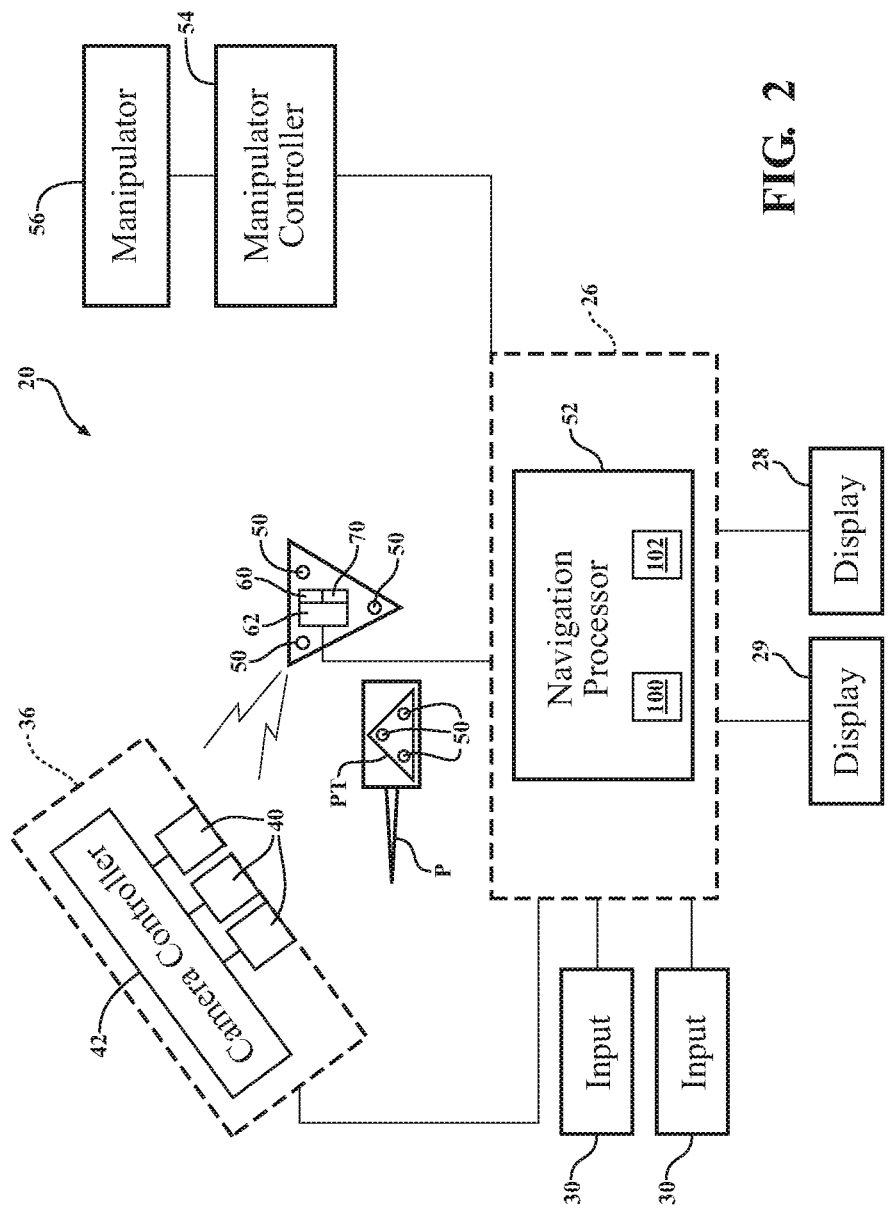
FIG. 2 is a schematic view of the navigation system.

Referring to FIG. 2, each of the LEDs 50 are connected to a tracker controller 62 located in a housing (not shown) of the associated tracker 44, 46, 48 that transmits/receives data to/from the navigation computer 26. In one embodiment, the tracker controllers 62 transmit data on the order of several Megabytes/second through wired connections with the navigation computer 26. In other embodiments, a wireless connection may be used. In these embodiments, the navigation computer 26 has a transceiver (not shown) to receive the data from the tracker controller 62.

In other embodiments, the trackers 44, 46, 48 may have passive markers (not shown), such as reflectors that reflect light emitted from the camera unit 36. The reflected light is then received by the optical sensors 40. Active and passive arrangements are well known in the art.

Each of the trackers 44, 46, 48 also includes a 3-dimensional gyroscope sensor 60 that measures angular velocities of the trackers 44, 46, 48. As is well known to those skilled in the art, the gyroscope sensors 60 output readings indicative of the angular velocities relative to x-, y-, and z-axes of a gyroscope coordinate system. These readings are multiplied by a conversion constant defined by the manufacturer to obtain measurements in degrees/second with respect to each of the x-, y-, and z-axes of the gyroscope coordinate system. These measurements can then be converted to an angular velocity vector $\vec{\omega}$ defined in radians/second.

The angular velocities measured by the gyroscope sensors 60 provide additional non-optically based kinematic data for the navigation system 20 with which to track the trackers 44, 46, 48. The gyroscope sensors 60 may be oriented along the axis of each coordinate system of the trackers 44, 46, 48. In other embodiments, each gyroscope coordinate system is transformed to its tracker coordinate system such that the gyroscope data reflects the angular velocities with respect to the x-, y-, and z-axes of the coordinate systems of the trackers 44, 46, 48.

Each of the gyroscope sensors 60 communicate with the tracker controller 62 located within the housing of the associated tracker that transmits/receives data to/from the navigation computer 26. The navigation computer 26 has one or more transceivers (not shown) to receive the data from the gyroscope sensors 60. The data can be received either through a wired or wireless connection.

The gyroscope sensors 60 preferably have sampling rates of 100 Hz or more, more preferably 300 Hz or more, and most preferably 500 Hz or more. In some embodiments, the gyroscope sensors 60 have sampling rates of 1000 Hz. The sampling rate of the gyroscope sensors 60 is the rate at which signals are sent out from the gyroscope sensors 60 to be converted into angular velocity data.

The sampling rates of the gyroscope sensors 60 and the optical sensors 40 are established or timed so that for each optical measurement of position there is a corresponding non-optical measurement of angular velocity.

Each of the trackers 44, 46, 48 also includes a 3-axis accelerometer 70 that measures acceleration along each of x-, y-, and z-axes of an accelerometer coordinate system. The accelerometers 70 provide additional non-optically based data for the navigation system 20 with which to track the trackers 44, 46, 48.

Each of the accelerometers 70 communicate with the tracker controller 62 located in the housing of the associated tracker that transmits/receives data to/from the navigation computer 26. One or more of the transceivers (not shown) of the navigation computer receives the data from the accelerometers 70.

The accelerometers 70 may be oriented along the axis of each coordinate system of the trackers 44, 46, 48. In other embodiments, each accelerometer coordinate system is transformed to its tracker coordinate system such that the accelerometer data reflects the accelerations with respect to the x-, y-, and z-axes of the coordinate systems of the trackers 44, 46, 48.

The navigation computer 26 includes a navigation processor 52. The camera unit 36 receives optical signals from the LEDs 50 of the trackers 44, 46, 48 and outputs to the processor 52 signals relating to the position of the LEDs 50 of the trackers 44, 46, 48 relative to the localizer 34. The gyroscope sensors 60 transmit non-optical signals to the processor 52 relating to the 3-dimensional angular velocities measured by the gyroscope sensors 60. Based on the received optical and non-optical signals, navigation processor 52 generates data indicating the relative positions and orientations of the trackers 44, 46, 48 relative to the localizer 34.

It should be understood that the navigation processor 52 could include one or more processors to control operation of the navigation computer 26. The processors can be any type of microprocessor or multi-processor system. The term processor is not intended to limit the scope of the invention to a single processor.

Prior to the start of the surgical procedure, additional data are loaded into the navigation processor 52. Based on the position and orientation of the trackers 44, 46, 48 and the previously loaded data, navigation processor 52 determines the position of the working end of the surgical instrument 22 and the orientation of the surgical instrument 22 relative to the tissue against which the working end is to be applied. In some embodiments, navigation processor 52 forwards these data to a manipulator controller 54. The manipulator controller 54 can then use the data to control a robotic manipulator 56 as described in U.S. Provisional Patent Application No. 61/679,258, entitled, "Surgical Manipulator Capable of Controlling a Surgical Instrument in either a Semi-Autonomous Mode or a Manual, Boundary Constrained Mode, the disclosure of which is hereby incorporated by reference, and also in U.S. patent application Ser. No. 13/958,834, entitled, "Navigation System for use with a Surgical Manipulator Operable in Manual or Semi-Autonomous Mode", the disclosure of which is hereby incorporated by reference.

The navigation processor 52 also generates image signals that indicate the relative position of the surgical instrument working end to the surgical site. These image signals are applied to the displays 28, 29. Displays 28, 29, based on these signals, generate images that allow the surgeon and staff to view the relative position of the surgical instrument working end to the surgical site. The displays, 28, 29, as discussed above, may include a touch screen or other input/output device that allows entry of commands.

II. Coordinate Systems and Transformation

Figure 3:
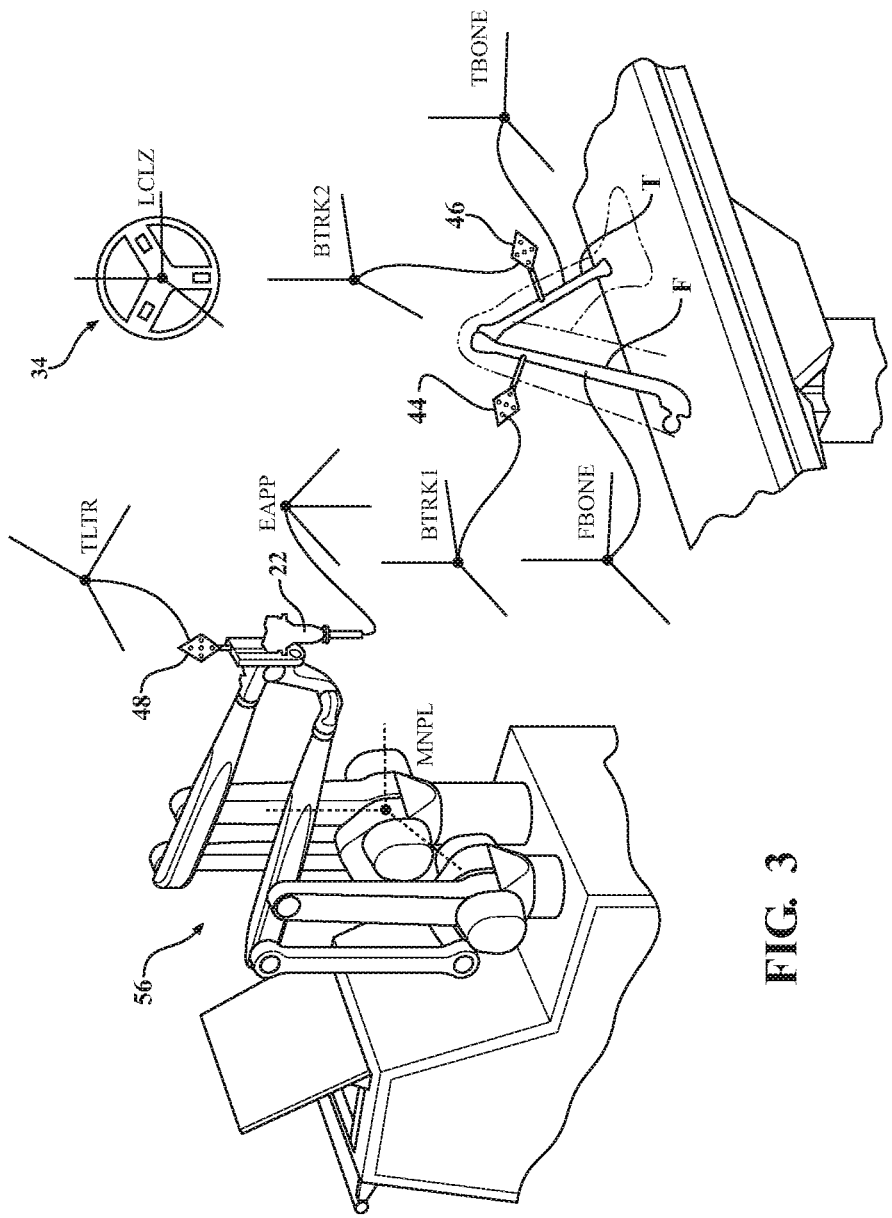
FIG. 3 is schematic view of coordinate systems used with the navigation system.

Referring to FIG. 3, tracking of objects is generally conducted with reference to a localizer coordinate system LCLZ. The localizer coordinate system has an origin and an orientation (a set of x-, y-, and z-axes). During the procedure one goal is to keep the localizer coordinate system LCLZ stationary. As will be described further below, an accelerometer mounted to the camera unit 36 may be used to track sudden or unexpected movement of the localizer coordinate system LCLZ, as may occur when the camera unit 36 is inadvertently bumped by surgical personnel.

Each tracker 44, 46, 48 and object being tracked also has its own coordinate system separate from localizer coordinate system LCLZ. Components of the navigation system 20 that have their own coordinate systems are the bone trackers 44, 46 and the instrument tracker 48. These coordinate systems are represented as, respectively, bone tracker coordinate systems BTRK1, BTRK2, and instrument tracker coordinate system TLTR.

Navigation system 20 monitors the positions of the femur F and tibia T of the patient by monitoring the position of bone trackers 44, 46 firmly attached to bone. Femur coordinate system is FBONE and tibia coordinate system is TBONE, which are the coordinate systems of the bones to which the bone trackers 44, 46 are firmly attached.

Prior to the start of the procedure, pre-operative images of the femur F and tibia T are generated (or of other tissues in other embodiments). These images may be based on MRI scans, radiological scans or computed tomography (CT) scans of the patient's anatomy. These images are mapped to the femur coordinate system FBONE and tibia coordinate system TBONE using well known methods in the art. In one embodiment, a pointer instrument P, such as disclosed in U.S. Pat. No. 7,725,162 to Malackowski, et al., hereby incorporated by reference, having its own tracker PT (see FIG. 2), may be used to map the femur coordinate system FBONE and tibia coordinate system TBONE to the pre-operative images. These images are fixed in the femur coordinate system FBONE and tibia coordinate system TBONE.

During the initial phase of the procedure, the bone trackers 44, 46 are firmly affixed to the bones of the patient. The pose (position and orientation) of coordinate systems FBONE and TBONE are mapped to coordinate systems BTRK1, BTRK2, respectively. Given the fixed relationship between the bones and their bone trackers 44, 46, the pose of coordinate systems FBONE and TBONE remain fixed relative to coordinate systems BTRK1, BTRK2, respectively, throughout the procedure. The pose-describing data are stored in memory integral with both manipulator controller 54 and navigation processor 52.

The working end of the surgical instrument 22 (also referred to as energy applicator distal end) has its own coordinate system EAPP. The origin of the coordinate system EAPP may represent a centroid of a surgical cutting bur, for example. The pose of coordinate system EAPP is fixed to the pose of instrument tracker coordinate system TLTR before the procedure begins. Accordingly, the poses of these coordinate systems EAPP, TLTR relative to each other are determined. The pose-describing data are stored in memory integral with both manipulator controller 54 and navigation processor 52.

III. Software

Referring to FIG. 2, a localization engine 100 is a software module that can be considered part of the navigation system 20. Components of the localization engine 100 run on navigation processor 52. In some versions of the invention, the localization engine 100 may run on the manipulator controller 54.

Localization engine 100 receives as inputs the optically-based signals from the camera controller 42 and the non-optically based signals from the tracker controller 62. Based on these signals, localization engine 100 determines the pose (position and orientation) of the bone tracker coordinate systems BTRK1 and BTRK2 in the localizer coordinate system LCLZ. Based on the same signals received for the instrument tracker 48, the localization engine 100 determines the pose of the instrument tracker coordinate system TLTR in the localizer coordinate system LCLZ.

The localization engine 100 forwards the signals representative of the poses of trackers 44, 46, 48 to a coordinate transformer 102. Coordinate transformer 102 is a navigation system software module that runs on navigation processor 52. Coordinate transformer 102 references the data that defines the relationship between the pre-operative images of the patient and the patient trackers 44, 46. Coordinate transformer 102 also stores the data indicating the pose of the working end of the surgical instrument relative to the instrument tracker 48.

During the procedure, the coordinate transformer 102 receives the data indicating the relative poses of the trackers 44, 46, 48 to the localizer 34. Based on these data and the previously loaded data, the coordinate transformer 102 generates data indicating the relative position and orientation of both the coordinate system EAPP, and the bone coordinate systems, FBONE and TBONE to the localizer coordinate system LCLZ.

As a result, coordinate transformer 102 generates data indicating the position and orientation of the working end of the surgical instrument 22 relative to the tissue (e.g., bone) against which the instrument working end is applied. Image signals representative of these data are forwarded to displays 28, 29 enabling the surgeon and staff to view this information. In certain embodiments, other signals representative of these data can be forwarded to the manipulator controller 54 to control the manipulator 56 and corresponding movement of the surgical instrument 22.

Figure 4:
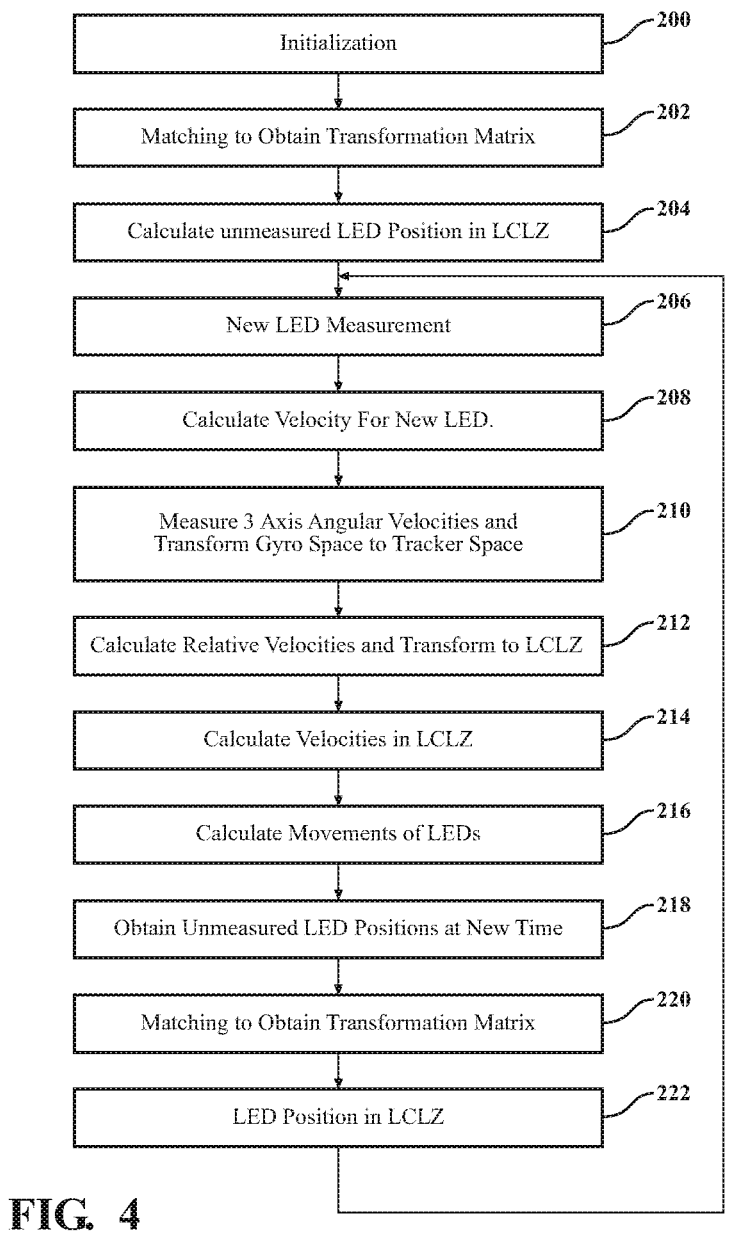
FIG. 4 is a flow diagram of steps carried out by a localization engine of the navigation system.

Steps for determining the pose of each of the tracker coordinate systems BTRK1, BTRK2, TLTR in the localizer coordinate system LCLZ are the same, so only one will be described in detail. The steps shown in FIG. 4 are based on only one tracker being active, tracker 44. In the following description, the LEDs of tracker 44 shall be represented by numerals 50a, 50b, 50c which identify first 50a, second 50b, and third 50c LEDs.

The steps set forth in FIG. 4 illustrate the use of optically-based sensor data and non-optically based sensor data to determine the positions of the LEDs 50a, 50b, 50c of tracker 44. From these positions, the navigation processor 52 can determine the position and orientation of the tracker 44, and thus, the position and orientation of the femur F to which it is attached. Optically-based sensor data derived from the signals received by the optical sensors 40 provide line-of-sight based data that relies on the line-of-sight between the LEDs 50a, 50b, 50c and the optical sensors 40. However, the gyroscope sensor 60, which provides non-optically based signals for generating non-optically based sensor data do not rely on line-of-sight and thus can be integrated into the navigation system 20 to better approximate positions of the LEDs 50a, 50b, 50c when two of the LEDs 50a, 50b, 50c are not being measured (since only one LED measured at a time), or when one or more of the LEDs 50a, 50b, 50c are not visible to the optical sensors 40 during a procedure.

In a first initialization step 200, the system 20 measures the position of the LEDs 50a, 50b, 50c for the tracker 44 in the localizer coordinate system LCLZ to establish initial position data. These measurements are taken by sequentially firing the LEDs 50a, 50b, 50c, which transmits light signals to the optical sensors 40. Once the light signals are received by the optical sensors 40, corresponding signals are generated by the optical sensors 40 and transmitted to the camera controller 42. The frequency between firings of the LEDs 50a, 50b, 50c is 100 Hz or greater, preferably 300 Hz or greater, and more preferably 500 Hz or greater. In some cases, the frequency between firings is 1000 Hz or 1 millisecond between firings.

In some embodiments, only one LED can be read by the optical sensors 40 at a time. The camera controller 42, through one or more infrared or RF transceivers (on camera unit 36 and tracker 44) may control the firing of the LEDs 50a, 50b, 50c, as described in U.S. Pat. No. 7,725,162 to Malackowski, et al., hereby incorporated by reference. Alternatively, the tracker 44 may be activated locally (such as by a switch on tracker 44) which then fires its LEDs 50a, 50b, 50c sequentially once activated, without instruction from the camera controller 42.

Based on the inputs from the optical sensors 40, the camera controller 42 generates raw position signals that are then sent to the localization engine 100 to determine the position of each of the corresponding three LEDs 50a, 50b, 50c in the localizer coordinate system LCLZ.

During the initialization step 200, in order to establish the initial position data, movement of the tracker 44 must be less than a predetermined threshold. A value of the predetermined threshold is stored in the navigation computer 26. The initial position data established in step 200 essentially provides a static snapshot of position of the three LEDs 50a, 50b, 50c at an initial time t0, from which to base the remaining steps of the process. During initialization, velocities of the LEDs 50a, 50b, 50c are calculated by the localization engine 100 between cycles (i.e., each set of three LED measurements) and once the velocities are low enough, i.e., less than the predetermined threshold showing little movement occurred, then the initial position data or static snapshot is established. In some embodiments, the predetermined threshold (also referred to as the static velocity limit) is 200 mm/s or less, preferably 100 mm/s or less, and more preferably 10 mm/s or less along any axis. When the predetermined threshold is 100 mm/s, then the calculated velocities must be less than 100 mm/s to establish the static snapshot.

Referring to FIGS. 4 and 4A, once the static snapshot is taken, the positions of the measured LEDs 50a, 50b, 50c are compared to a model of the tracker 44 in step 202. The model is data stored in the navigation computer 26. The model data indicates the positions of the LEDs on the tracker 44 in the tracker coordinate system BTRK1. The system 20 has stored the number and position of the LEDs 50 of each tracker 44, 46, 48 in each tracker's coordinate system. For trackers 44, 46, 48 the origin of their coordinate systems is set at the centroid of all LED positions of the tracker 44.

The localization engine 100 utilizes a rigid body matching algorithm or point matching algorithm to match the measured LEDs 50a, 50b, 50c in the localizer coordinate system LCLZ to the LEDs in the stored model. Once the best-fit is determined, the localization engine 100 evaluates the deviation of the fit to determine if the measured LEDs 50a, 50b, 50c fit within a stored predefined tolerance of the model. The tolerance may be based on a distance between the corresponding LEDs such that if the fit results in too great of a distance, the initialization step has to be repeated. In some embodiments, the positions of the LEDs must not deviate from the model by more than 2.0 mm, preferably not more than 0.5 mm, and more preferably not more than 0.1 mm.

If the fit is within the predefined tolerance, a transformation matrix is generated to transform any other unmeasured LEDs in the model from the bone tracker coordinate system BTRK1 into the localizer coordinate system LCLZ in step 204. This step is utilized if more than three LEDs are used or if virtual LEDs are used as explained further below. In some embodiments, trackers 44, 46, 48 may have four or more LEDs. Once all positions in the localizer coordinate system LCLZ are established, an LED cloud is created. The LED cloud is an arrangement of all LEDs 50a, 50b, 50c on the tracker 44 in the localizer coordinate system LCLZ based on the x-, y-, and z-axis positions of all the LEDs 50a, 50b, 50c in the localizer coordinate system LCLZ.

Once the LED cloud is initially established, the navigation system 20 can proceed with tracking the tracker 44 during a surgical procedure. As previously discussed, this includes firing the next LED in the sequence. For illustration, LED 50a is now fired. Thus, LED 50a transmits light signals to the optical sensors 40. Once the light signals are received by the optical sensors 40, corresponding signals are generated by the optical sensors 40 and transmitted to the camera controller 42.

Based on the inputs from the optical sensors 40, the camera controller 42 generates a raw position signal that is then sent to the localization engine 100 to determine at time t1 the new position of LED 50a relative to the x-, y-, and z-axes of the localizer coordinate system LCLZ. This is shown in step 206 as a new LED measurement.

It should be appreciated that the designation of time such as t0, t1 . . . tn is used for illustrative purposes to indicate different times or different ranges of time or time periods and does not limit this invention to specific or definitive times.

With the new position of LED 50a determined, a linear velocity vector of LED 50a can be calculated by the localization engine 100 in step 208.

The tracker 44 is treated as a rigid body. Accordingly, the linear velocity vector of LED 50a is a vector quantity, equal to the time rate of change of its linear position. The velocity, even the acceleration of each LED, in localizer coordinate system LCLZ, can be calculated from the previously and currently measured positions and time of that LED in localizer coordinate system LCLZ. The previously and currently measured positions and time of a LED define the position history of that LED. The velocity calculation of LED 50a can take the simplest form of:

$$\vec{v}(LED50a) = \frac{\vec{x}_n - \vec{x}_p}{t_n - t_p}$$

Where $\vec{x}_p = (x, y, z)_p$ and is the previously measured position of LED 50a at time $t_p$; and $\vec{x}_n = (x, y, z)_n$ and is the currently measured position of LED 50a at time $t_n$. One can also obtain the velocity and/or acceleration of each LED by data fitting the LED position history of that LED as is well known to those skilled in the art.

At time t1, in step 210, the gyroscope sensor 60 is also measuring an angular velocity of the tracker 44. Gyroscope sensor 60 transmits signals to the tracker controller 62 related to this angular velocity.

The tracker controller 62 then transmits a corresponding signal to the localization engine 100 so that the localization engine 100 can calculate an angular velocity vector $\vec{\omega}$ from these signals. In step 210, the gyroscope coordinate system is also transformed to the bone tracker coordinate system BTRK1 so that the angular velocity vector $\vec{\omega}$ calculated by the localization engine 100 is expressed in the bone tracker coordinate system BTRK1.

In step 212, a relative velocity vector $\vec{v}R$ is calculated for the origin of the bone tracker coordinate system BTRK1 with respect to position vector $\vec{x}$ (LED50a to ORIGIN). This position vector $\vec{x}$ (LED50a to ORIGIN) is also stored in memory in the navigation computer 26 for access by the localization engine 100 for the following calculation. This calculation determines the relative velocity of the origin $\vec{v}R$ (ORIGIN) of the bone tracker coordinate system BTRK1 by calculating the cross product of the angular velocity vector $\vec{\omega}$ derived from the gyroscope signal and the position vector from LED 50a to the origin.

$$\vec{v}R \text{ (ORIGIN)} = \vec{\omega} \times \vec{x} \text{ (LED50a to ORIGIN)}$$

The localization engine 100 then calculates relative velocity vectors $\vec{v}R$ for the remaining, unmeasured LEDs 50b, 50c (unmeasured because these LEDs have not been fired and thus their positions are not being measured). These velocity vectors can be calculated with respect to the origin of bone tracker coordinate system BTRK1.

The calculation performed by the localization engine 100 to determine the relative velocity vector $\vec{v}R$ for each unmeasured LED 50b, 50c at time t1 is based on the cross product of the angular velocity vector $\vec{\omega}$ at time t1 and the position vectors $\vec{x}$ (ORIGIN to LED50b) and $\vec{x}$ (ORIGIN to LED50c), which are taken from the origin of bone tracker coordinate system BTRK1 to each of the unmeasured LEDs 50b, 50c. These position vectors $\vec{x}$ (ORIGIN to LED50b) and $\vec{x}$ (ORIGIN to LED50c) are stored in memory in the navigation computer 26 for access by the localization engine 100 for the following calculations:

$$\vec{v}R \text{ (LED50b)} = \vec{\omega} \times \vec{x} \text{ (ORIGIN to LED50b)}$$

$$\vec{v}R \text{ (LED50c)} = \vec{\omega} \times \vec{x} \text{ (ORIGIN to LED50c)}$$

Also in step 212, these relative velocities, which are calculated in the bone tracker coordinate system BTRK1, are transferred into the localizer coordinate system LCLZ using the transformation matrix determined in step 202. The relative velocities in the localizer coordinate system LCLZ are used in calculations in step 214.

In step 214 the velocity vector $\vec{v}$ of the origin of the bone tracker coordinate system BTRK1 in the localizer coordinate system LCLZ at time t1 is first calculated by the localization engine 100 based on the measured velocity vector $\vec{v}$ (LED50a) of LED 50a at time t1. The velocity vector $\vec{v}$ (ORIGIN) is calculated by adding the velocity vector $\vec{v}$ (LED50a) of LED 50a at time t1 and the relative velocity vector $\vec{v}R$ (ORIGIN) of the origin at time t1 expressed relative to the position vector of LED 50a to the origin. Thus, the velocity vector of the origin at time t1 is calculated as follows:

$$\vec{v}\text{ (ORIGIN)}=\vec{v}\text{ (LED50}a\text{)}+\vec{v}R\text{ (ORIGIN)}$$

Velocity vectors of the remaining, unmeasured LEDs in the localizer coordinate system LCLZ at time t1 can now be calculated by the localization engine 100 based on the velocity vector $\vec{v}$ (ORIGIN) of the origin of the bone tracker coordinate system BTRK1 in the localizer coordinate system LCLZ at time t1 and their respective relative velocity vectors at time t1 expressed relative to their position vectors with the origin of the bone tracker coordinate system BTRK1. These velocity vectors at time t1 are calculated as follows:

$$\vec{v}\text{ (LED50}b\text{)}=\vec{v}\text{ (ORIGIN)}+\vec{v}r\text{ (LED50}b\text{)}$$

$$\vec{v}\text{ (LED50}c\text{)}=\vec{v}\text{ (ORIGIN)}+\vec{v}r\text{ (LED50}c\text{)}$$

In step 216, the localization engine 100 calculates the movements, i.e., the change in position Δx (in Cartesian coordinates), of each of the unmeasured LEDs 50b, 50c from time t0 to time t1 based on the calculated velocity vectors of LEDs 50b, 50c and the change in time. In some embodiments the change in time Δt for each LED measurement is two milliseconds or less, and in some embodiments one millisecond or less.

$$\Delta x\text{ (LED50}b\text{)}=\vec{v}\text{ (LED50}b\text{)}\times\Delta t$$

$$\Delta x\text{ (LED50}c\text{)}=\vec{v}\text{ (LED50}c\text{)}\times\Delta t$$

These calculated changes in position (x, y, z) can then be added to the previously determined positions of each of LEDs 50b, 50c in the localizer coordinate system LCLZ. Thus, in step 218, changes in position can be added to the previous positions of the LEDs 50b, 50c at time t0, which were determined during the static snapshot. This is expressed as follows:

$$x\text{ (LED50}b\text{)}_{t1}=x\text{ (LED50}b\text{)}_{t0}+\Delta x\text{ (LED50}b\text{)}$$

In step 220, these calculated positions for each of LEDs 50b, 50c at time t1 are combined with the determined position of LED 50a at time t1. The newly determined positions of LEDs 50a, 50b, 50c are then matched to the model of tracker 44 to obtain a best fit using the point matching algorithm or rigid body matching algorithm. The result of this best fit calculation, if within the defined tolerance of the system 20, is that a new transformation matrix is created by the navigation processor 52 to link the bone tracker coordinate system BTRK1 to the localizer coordinate system LCLZ.

With the new transformation matrix the newly calculated positions of the unmeasured LEDs 50b, 50c are adjusted to the model in step 222 to provide adjusted positions. The measured position of LED 50a can also be adjusted due to the matching algorithm such that it is also recalculated. These adjustments are considered an update to the LED cloud. In some embodiments, the measured position of LED 50a is fixed to the model's position of LED 50a during the matching step.

With the best fit transformation complete, the measured (and possibly adjusted) position of LED 50a and the calculated (and adjusted) positions of LEDs 50b, 50c in the localizer coordinate system LCLZ enable the coordinate transformer 102 to determine a new position and orientation of the femur F based on the previously described relationships between the femur coordinate system FBONE, the bone tracker coordinate system BTRK1, and the localizer coordinate system LCLZ.

Steps 206 through 222 are then repeated at a next time t2 and start with the measurement in the localizer coordinate system LCLZ of LED 50b, with LEDs 50a, 50c being the unmeasured LEDs. As a result of this loop at each time t1, t2 . . . tn positions of each LED 50a, 50b, 50c are either measured (one LED being fired at each time) or calculated with the calculated positions being very accurately approximated based on measurements by the optical sensor 40 and the gyroscope sensor 60. This loop of steps 206 through 222 to determine the new positions of the LEDs 50 can be carried out by the localization engine 100 at a frequency of at least 100 Hz, more preferably at least 300 Hz, and most preferably at least 500 Hz.

Figure 5:
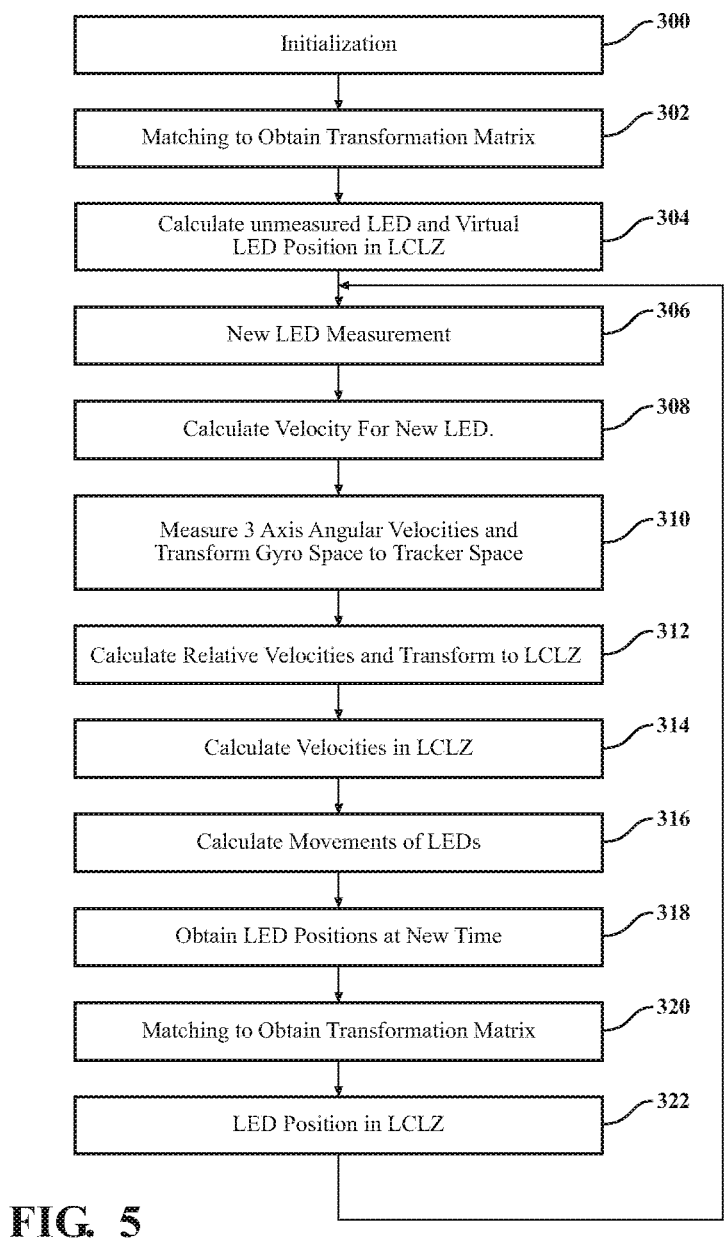
FIG. 5 is a flow diagram of steps carried out by the localization engine in a first alternative embodiment.

Referring to FIG. 5, the LED cloud may also include virtual LEDs, which are predetermined points identified on the model, but that do not actually correspond to physical LEDs on the tracker 44. The positions of these points may also be calculated at times t1, t2 . . . tn. These virtual LEDs can be calculated in the same fashion as the unmeasured LEDs with reference to FIG. 4. The only difference is that the virtual LEDs are never fired or included in the sequence of optical measurements, since they do not correspond to any light source, but are merely virtual in nature. Steps 300-322 show the steps used for tracking the trackers 44, 46, 48 using real and virtual LEDS. Steps 300-322 generally correspond to steps 200-222 except for the addition of the virtual LEDs, which are treated like unmeasured LEDs using the same equations described above.

One purpose of using virtual LEDs in addition to the LEDs 50a, 50b, 50c, for example, is to reduce the effect of errors in the velocity calculations described above. These errors may have little consequence on the calculated positions of the LEDs 50a, 50b, 50c, but can be amplified the further away from the LEDs 50a, 50b, 50c a point of interest is located. For instance, when tracking the femur F with tracker 44, the LEDs 50a, 50b, 50c incorporated in the tracker 44 may experience slight errors in their calculated positions of about 0.2 millimeters. However, consider the surface of the femur F that may be located over 10 centimeters away from the LEDs 50a, 50b, 50c. The slight error of 0.2 millimeters at the LEDs 50a, 50b, 50c can result in 0.4 to 2 millimeters of error on the surface of the femur F. The further away the femur F is located from the LEDs 50a, 50b, 50c the more the error increases. The use of virtual LEDs in the steps of FIG. 5 can reduce the potential amplification of such errors as described below.

Figure 5A:
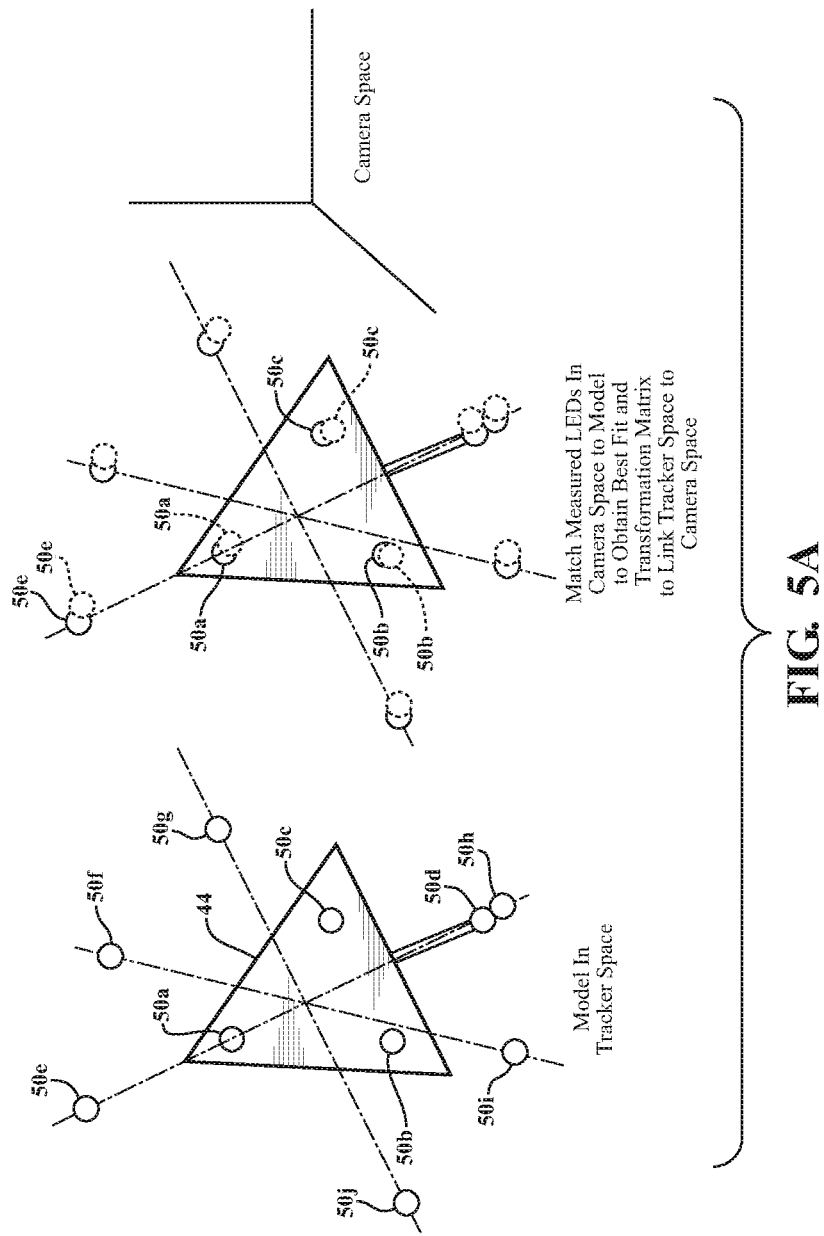
FIG. 5A is an illustration of a tracker model including real and virtual LEDs.

Referring to FIG. 5A, one virtual LED 50d can be positioned on the surface of the femur F. Other virtual LEDs 50e, 50f, 50g, 50h, 50i, 50j, 50k can be positioned at random locations in the bone tracker coordinate system BTRK1 such as along each of the x-, y-, and z-axes, and on both sides of the origin along these axes to yield 6 virtual LEDs. These virtual LEDs are included as part of the model of the tracker 44 shown in FIG. 5A and used in steps 302 and 320. In some embodiments, only the virtual LEDs 50e-50k are used. In other embodiments, virtual LEDs may be positioned at locations along each of the x-, y-, and z-axes, but at different distances from the origin of the bone tracker coordinate system BTRK1. In still further embodiments, some or all of the virtual LEDs may be located off of the axes x-, y-, and z-.

Now in the model are real LEDs 50a, 50b, 50c and virtual LEDs 50d-50k. At each time t1, t2 . . . tn this extended model is matched in step 320 with the measured/calculated positions of real LEDs 50a, 50b, 50c and with the calculated positions of virtual LEDs 50d-50k to obtain the transformation matrix that links the bone tracker coordinate system BTRK1 with the localizer coordinate system LCLZ. Now, with the virtual LEDs 50d-50k included in the model, which are located at positions outlying the real LEDs 50a, 50b, 50c, the error in the rotation matrix can be reduced. In essence, the rigid body matching algorithm or point matching algorithm has additional points used for matching and some of these additional points are located radially outwardly from the points defining the real LEDs 50a, 50b, 50c, thus rotationally stabilizing the match.

In another variation of the process of FIG. 5, the locations of the virtual LEDs 50e-50k can be changed dynamically during use depending on movement of the tracker 44. The calculated positions of the unmeasured real LEDs 50b, 50c and the virtual LEDs 50e-50k at time t1 are more accurate the slower the tracker 44 moves. Thus, the locations of virtual LEDs 50e-50k along the x-, y-, and z-axes relative to the origin of the bone tracker coordinate system BTRK1 can be adjusted based on speed of the tracker 44. Thus, if the locations of the virtual LEDs 50e-50k are denoted (s,0,0), (−s,0,0), (0,s,0), (0,−s,0), (0,0,s), (0,0,−s), respectively, then s would increase when the tracker 44 moves slowly and s would decrease to a smaller value when the tracker 44 moves faster. This could be handled by an empirical formula for s or s can be adjusted based on an estimate in the error in velocity and calculated positions.

Determining new positions of the LEDs 50 (real and virtual) can be carried out at a frequency of at least 100 Hz, more preferably at least 300 Hz, and most preferably at least 500 Hz.

Data from the accelerometers 70 can be used in situations where optical measurement of an LED 50 is impeded due to interference with the line-of-sight. When an LED to be measured is blocked, the localization engine 100 assumes a constant velocity of the origin to estimate positions. However, the constant velocity assumption in this situation may be inaccurate and result in errors. The accelerometers 70 essentially monitor if the constant velocity assumption in the time period is accurate. The steps shown in FIGS. 6 and 7 illustrate how this assumption is checked.

Figure 6:
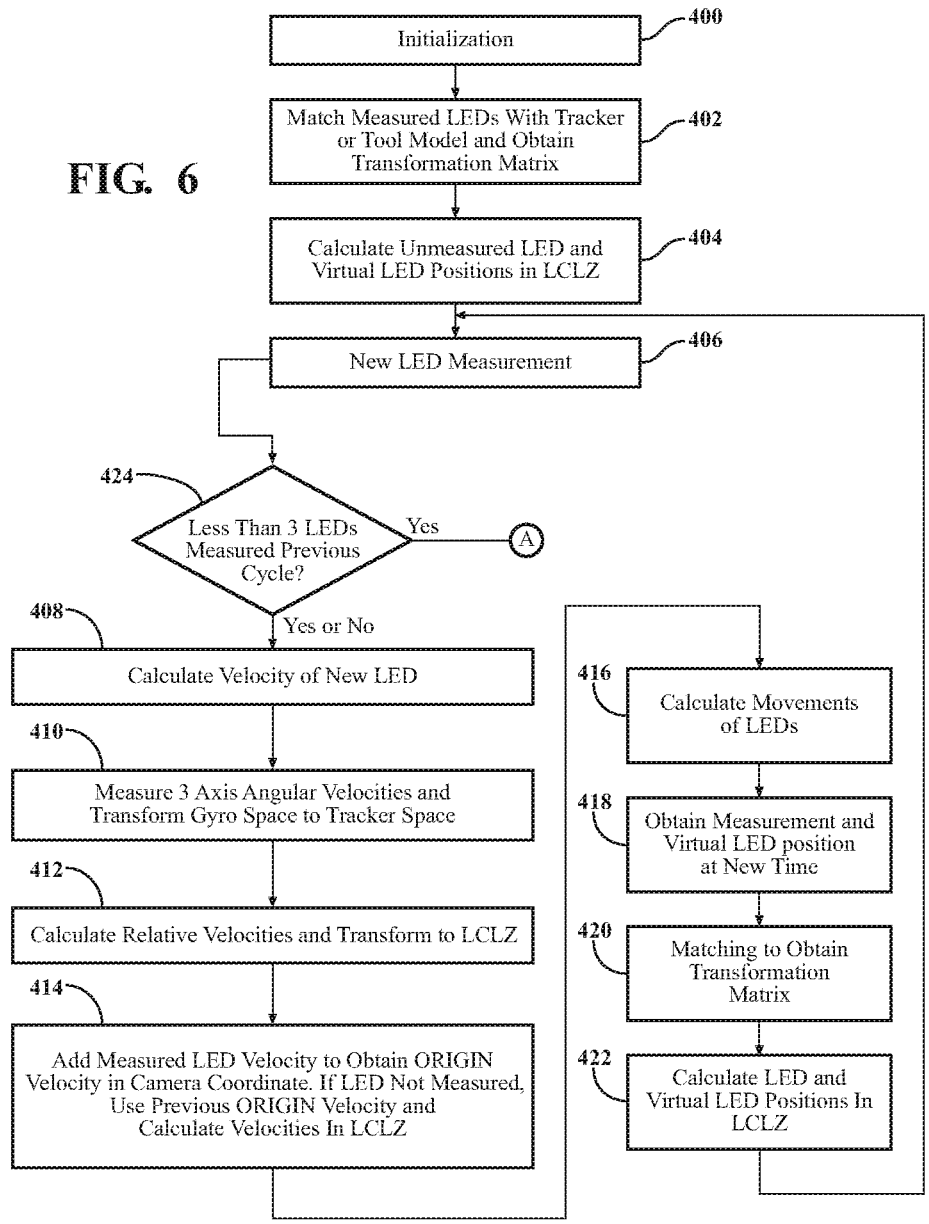
FIG. 6 is a flow diagram of steps carried out by the localization engine in a second alternative embodiment.
Figure 7:
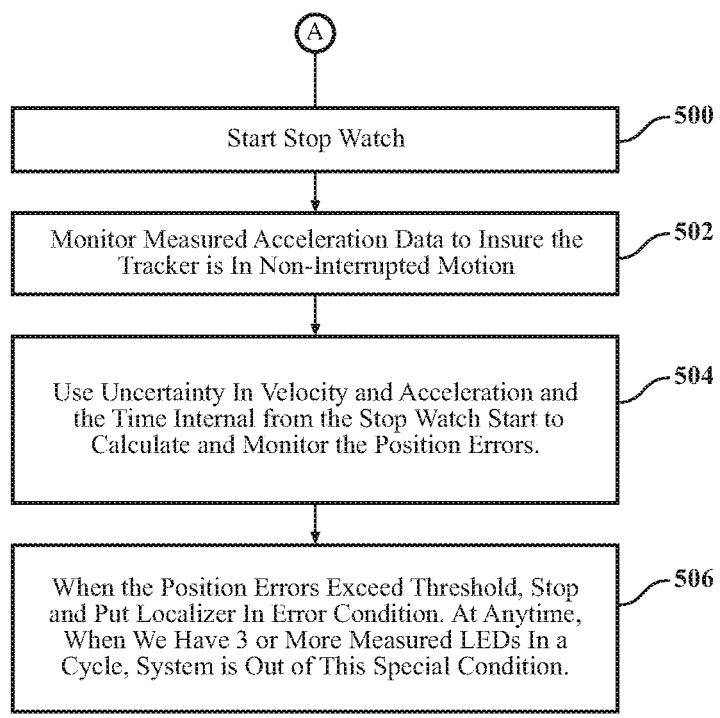
FIG. 7 is a flow diagram of steps carried out by the localization engine when one or more LEDs are blocked from measurement.

Continuing to use tracker 44 as an example, steps 400-422 of FIG. 6 generally correspond to steps 300-322 from FIG. 5. However, in step 424, the system 20 determines whether, in the last cycle of measurements, less than 3 LEDs were measured—meaning that one or more of the LEDs in the cycle could not be measured. This could be caused by line-of-sight issues, etc. A cycle for tracker 44 is the last three attempted measurements. If during the last three measurements, each of the LEDs 50a, 50b, 50c were visible and could be measured, then the system 20 proceeds to step 408 and continues as previously described with respect to FIG. 5.

If the system 20 determines that one or more of the LEDs 50a, 50b, 50c could not be measured during the cycle, i.e., were blocked from measurement, then the algorithm still moves to step 408, but if the new LED to be measured in step 406 was the one that could not be measured, the system makes some velocity assumptions as described below.

When a LED, such as LED 50a, is not seen by the optical sensor 40 at its measurement time to in step 406, the previously calculated velocity vector $\vec{v}$ (ORIGIN) of the origin of the tracker 44 in the localizer coordinate system LCLZ at the previous time t(n−1) is assumed to remain constant. Accordingly, velocity vectors of LEDs 50a, 50b, 50c in the localizer coordinate system LCLZ can be calculated based on the previously calculated velocity vector $\vec{v}$ (ORIGIN) in the localizer coordinate system LCLZ and the relative velocity vectors of LEDs 50a, 50b, 50c, which are derived from a newly measured angular velocity vector from the gyroscope 60. The equations described in steps 316-322 can then be used to determine new positions of the LEDs 50a, 50b, 50c.

To start, when LED 50a is to be measured at step 406, but is obstructed, the velocity vector of the origin is assumed to be the same as the previous calculation. Accordingly, the velocity of the new LED is not calculated at step 408:

$$\vec{v} \text{ (ORIGIN)=previous calculation}$$

Step 410 proceeds the same as step 310.

The relative velocity vectors $\vec{v}R$ of LEDs 50a, 50b, 50c calculated in step 412 are then based on the previous velocity vector $\vec{v}$ (ORIGIN) and the newly measured angular velocity vector from the gyroscope 60 in the bone tracker coordinate system BTRK1:

$$\vec{v}R \text{ (LED50}a\text{)}=\vec{\omega} \text{ (current)} \times \vec{x} \text{ (ORIGIN to LED50}a\text{)}$$

$$\vec{v}R \text{ (LED50}b\text{)}=\vec{\omega} \text{ (current)} \times \vec{x} \text{ (ORIGIN to LED50}b\text{)}$$

$$\vec{v}R \text{ (LED50}c\text{)}=\vec{\omega} \text{ (current)} \times \vec{x} \text{ (ORIGIN to LED50}c\text{)}$$

In step 414, velocity vectors in the localizer coordinate system LCLZ can the be calculated using the origin velocity vector $\vec{v}$ (ORIGIN) and the relative velocity vectors $\vec{v}R$ of LEDs 50a, 50b, 50c:

$$\vec{v} \text{ (LED50}a\text{)}=\vec{v} \text{ (ORIGIN)}+\vec{v}R \text{ (LED50}a\text{)}$$

$$\vec{v} \text{ (LED50}b\text{)}=\vec{v} \text{ (ORIGIN)}+\vec{v}R \text{ (LED50}b\text{)}$$

$$\vec{v} \text{ (LED50}c\text{)}=\vec{v} \text{ (ORIGIN)}+\vec{v}R \text{ (LED50}c\text{)}$$

Steps 416 through 422 proceed the same as steps 316-322.

If the system 20 determines at step 424 that one or more of the LEDs 50a, 50b, 50c could not be measured during the cycle, i.e., were blocked from measurement, another algorithm is carried out simultaneously at steps 500-506 shown in FIG. 7 until a complete cycle of measurements is made where all of the LEDs 50a, 50b, 50c in the cycle were visible to the optical sensor 40. Thus, the system 20 is considered to be in a "blocked" condition until the complete cycle with all visible measurements is made.

Steps 500-506 are carried out continuously while the system 20 is in the blocked condition.

In step 500 the navigation processor 52 starts a clock that tracks how long the system 20 is in the blocked condition. The time in the blocked condition is referred to below as t (blocked).

In step 502, the accelerometer 70 measures accelerations along the x-, y-, and z-axes of the bone tracker coordinate system BTRK1 to track errors in the constant velocity assumption. Accelerometer readings, like gyroscope readings are transformed from the accelerometer coordinate system to the bone tracker coordinate system BTRK1.

If the accelerometer 70 detects acceleration(s) that exceed predefined acceleration tolerance(s), the navigation computer 26 will put the system 20 into an error condition. The acceleration tolerances could be defined differently along each x-, y-, and z-axis, or could be the same along each axis. If a measured acceleration exceeds a tolerance then the constant velocity assumption is unreliable and cannot be used for that particular application of surgical navigation. Different tolerances may be employed for different applications. For instance, during robotic cutting, the tolerance may be very low, but for visual navigation only, i.e., not feedback for cutting control loop, the tolerance may be set higher.

In step 504, velocity errors associated with the positions of the LEDs 50 relative to the optical sensor 40 are taken into account and monitored during the blocked condition. For each of the LEDs 50, the velocity $v_{error}$, multiplied by the time in the blocked condition $t_{blocked\ condition}$ must be less than a position error tolerance γ and thus must satisfy the following equation to prevent the system 20 from being put into an error condition:

$$v_{error} \times t_{blocked\ condition} \leq \gamma$$

In this equation, the velocity $v_{error}$ is calculated for each of the LEDs 50a, 50b, 50c as follows:

$$v_{error} = \frac{x_{error(t)} + x_{error(t-1)}}{\Delta t}$$

Position errors $x_{error(t)}$ and $x_{error(t-1)}$ are predefined position errors in the system 20 that are based on location relative to the optical sensors 40 at times t and t−1. In essence, the further away the LEDs 50a, 50b, 50c are located from the optical sensors 40, the higher the potential position errors. These positions errors are derived either experimentally or theoretically and placed in a look-up table or formula so that at each position of the LEDs 50a, 50b, 50c in Cartesian coordinates (x, y, z) an associated position error is provided.

In step 504, the localization engine 100 accesses this look-up table or calculates this formula to determine the position errors for each of LEDs 50a, 50b, 50c at the current time t and at the previous time t−1. The position errors are thus based on the positions in Cartesian coordinates in the localizer coordinate system LCLZ calculated by the system 20 in step 422 for the current time t and at the previous time t−1. The time variable Δt represents the time it takes for subsequent position calculations, so the difference between t and t−1, which for illustrative purposes may be 1 millisecond.

The position error tolerance γ is predefined in the navigation computer 26 for access by the localization engine 100. The position error tolerance γ could be expressed in millimeters. The position error tolerance γ can range from 0.001 to 1 millimeters and in some embodiments is specifically set at 0.5 millimeters. Thus, if the position error tolerance γ is set to 0.5 millimeters, the following equation must be satisfied:

$$v_{error} \times t_{blocked\ condition} < 0.5\ \text{millimeters}$$

As can be seen, the longer the system 20 is in the blocked condition, the larger the effect that the time variable has in this equation and thus the smaller the velocity errors that will be tolerated. In some embodiments, this equation is calculated by the localization engine 100 in step 504 separately for each of the LEDs 50a, 50b, 50c. In other embodiments, because of how closely arranged the LEDs 50a, 50b, 50c are on the tracker 44, the velocity error of only one of the LEDs 50a, 50b, 50c is used in this calculation to determine compliance.

In step 506, when the error(s) exceeds the position error tolerance γ, the system 20 is placed in an error condition. In such a condition, for example, any control or movement of cutting or ablation tools is ceased and the tools are shut down.

IV. Other Embodiments

In one embodiment, when each of the trackers 44, 46, 48 are being actively tracked, the firing of the LEDs occurs such that one LED from tracker 44 is fired, then one LED from tracker 46, then one LED from tracker 48, then a second LED from tracker 44, then a second LED from tracker 46, and so on until all LEDs have been fired and then the sequence repeats. This order of firing may occur through instruction signals sent from the transceivers (not shown) on the camera unit 36 to transceivers (not shown) on the trackers 44, 46, 48.

The navigation system 20 can be used in a closed loop manner to control surgical procedures carried out by surgical cutting instruments. Both the instrument 22 and the anatomy being cut are outfitted with trackers 50 such that the navigation system 20 can track the position and orientation of the instrument 22 and the anatomy being cut, such as bone.

In one embodiment, the navigation system is part of a robotic surgical system for treating tissue. In some versions, the robotic surgical system is a robotic surgical cutting system for cutting away material from a patient's anatomy, such as bone or soft tissue. The cutting system could be used to prepare bone for surgical implants such as hip and knee implants, including unicompartmental, bicompartmental, or total knee implants. Some of these types of implants are shown in U.S. patent application Ser. No. 13/530,927, entitled, "Prosthetic Implant and Method of Implantation", the disclosure of which is hereby incorporated by reference.

The robotic surgical cutting system includes a manipulator (see, for instance, FIG. 1). The manipulator has a plurality of arms and a cutting tool carried by at least one of said plurality of arms. A robotic control system controls or constrains movement of the cutting tool in at least 5 degrees of freedom. An example of such a manipulator and control system are shown in U.S. Provisional Patent Application No. 61/679,258, entitled, "Surgical Manipulator Capable of Controlling a Surgical Instrument in either a Semi-Autonomous Mode or a Manual, Boundary Constrained Mode", hereby incorporated by reference, and also in U.S. patent application Ser. No. 13/958,834, entitled, "Navigation System for use with a Surgical Manipulator Operable in Manual or Semi-Autonomous Mode", the disclosure of which is hereby incorporated by reference.

In this embodiment, the navigation system 20 communicates with the robotic control system (which can include the manipulator controller 54). The navigation system 20 communicates position and/or orientation data to said robotic control system. The position and/or orientation data is indicative of a position and/or orientation of instrument 22 relative to the anatomy. This communication provides closed loop control to control cutting of the anatomy such that the cutting occurs within a predefined boundary.

In this embodiment, manipulator movement may coincide with LED measurements such that for each LED measurement taken, there is a corresponding movement of the instrument 22 by the manipulator 56. However, this may not always be the case. For instance, there may be such a lag between the last LED measurement and movement by the manipulator 56 that the position and/or orientation data sent from the navigation computer 26 to the manipulator 56 for purposes of control loop movement becomes unreliable. In such a case, the navigation computer 26 can be configured to also transmit to the manipulator controller 54 kinematic data. Such kinematic data includes the previously determined linear and angular velocities for the trackers 44, 46, 48. Since the velocities are already known, positions can calculated based on the lag of time. The manipulator controller 54 could then calculate, for purposes of controlling movement of the manipulator 56, the positions and orientations of the trackers 44, 46, 48 and thus, the relative positions and orientations of the instrument 22 (or instrument tip) to the femur F and/or tibia T.

In this embodiment, the instrument 22 is held by the manipulator shown in FIG. 1 or other robot that provides some form of mechanical constraint to movement. This constraint limits the movement of the instrument 22 to within a predefined boundary. If the instrument 22 strays beyond the predefined boundary, a control is sent to the instrument 22 to stop cutting.

When tracking both the instrument 22 and the anatomy being cut in real time in these systems, the need to rigidly fix anatomy in position can be eliminated. Since both the instrument 22 and anatomy are tracked, control of the instrument 22 can be adjusted based on relative position and/or orientation of the instrument 22 to the anatomy. Also, representations of the instrument 22 and anatomy on the display can move relative to one another—to emulate their real world motion.

In one embodiment, each of the femur F and tibia T has a target volume of material that is to be removed by the working end of the surgical instrument 22. The target volumes are defined by one or more boundaries. The boundaries define the surfaces of the bone that should remain after the procedure. In some embodiments, system 20 tracks and controls the surgical instrument 22 to ensure that working end, e.g., bur, only removes the target volume of material and does not extend beyond the boundary, as disclosed in Provisional Patent Application No. 61/679,258, entitled, "Surgical Manipulator Capable of Controlling a Surgical Instrument in either a Semi-Autonomous Mode or a Manual, Boundary Constrained Mode", hereby incorporated by reference.

In the described embodiment, control of the instrument 22 is accomplished by utilizing the data generated by the coordinate transformer 102 that indicates the position and orientation of the bur or other cutting tool relative to the target volume. By knowing these relative positions, the surgical instrument 22 or the manipulator to which it is mounted, can be controlled so that only desired material is removed.

In other systems, the instrument 22 has a cutting tool that is movable in three degrees of freedom relative to a handheld housing and is manually positioned by the hand of the surgeon, without the aid of cutting jig, guide arm or other constraining mechanism. Such systems are shown in U.S. Provisional Patent Application No. 61/662,070, entitled, "Surgical Instrument Including Housing, a Cutting Accessory that Extends from the Housing and Actuators that Establish the Position of the Cutting Accessory Relative to the Housing", the disclosure of which is hereby incorporated by reference.

In these embodiments, the system includes a hand held surgical cutting instrument having a cutting tool. A control system controls movement of the cutting tool in at least 3 degrees of freedom using internal actuators/motors, as shown in U.S. Provisional Patent Application No. 61/662, 070, entitled, "Surgical Instrument Including Housing, a Cutting Accessory that Extends from the Housing and Actuators that Establish the Position of the Cutting Accessory Relative to the Housing", the disclosure of which is hereby incorporated by reference. The navigation system 20 communicates with the control system. One tracker (such as tracker 48) is mounted to the instrument. Other trackers (such as trackers 44, 46) are mounted to a patient's anatomy.

In this embodiment, the navigation system 20 communicates with the control system of the hand held surgical cutting instrument. The navigation system 20 communicates position and/or orientation data to the control system. The position and/or orientation data is indicative of a position and/or orientation of the instrument 22 relative to the anatomy. This communication provides closed loop control to control cutting of the anatomy such that the cutting occurs within a predefined boundary (the term predefined boundary is understood to include predefined trajectory, volume, line, other shapes or geometric forms, and the like).

Features of the invention may be used to track sudden or unexpected movements of the localizer coordinate system LCLZ, as may occur when the camera unit 36 is bumped by surgical personnel. An accelerometer (not shown) mounted to camera unit 36 monitors bumps and stops system 20 if a bump is detected. In this embodiment, the accelerometer communicates with the camera controller 42 and if the measured acceleration along any of the x, y, or z axes exceeds a predetermined value, then the camera controller 42 sends a corresponding signal to the navigation computer 26 to disable the system 20 and await the camera unit 36 to stabilize and resume measurements. In some cases, the initialization step 200, 300, 400 would have to be repeated before resuming navigation.

In some embodiments, a virtual LED is positioned at the working tip of the instrument 22. In this embodiment, the virtual LED is located at the location of the working tip in the model of the instrument tracker 48 so that the working tip location is continuously calculated.

It is an object of the intended claims to cover all such modifications and variations that come within the true spirit and scope of this invention. Furthermore, the embodiments described above are related to medical applications, but the inventions described herein are also applicable to other applications such as industrial, aerospace, defense, and the like.

What is claimed is:
1. A surgical system comprising:
   a robotic device configured to support a cutting tool and to move the cutting tool in at least three degrees of freedom;
   a control system configured to command the robotic device to control or constrain movement of the cutting tool;
   a first tracker configured to be coupled to the robotic device;
   a second tracker configured to be coupled to an anatomy and the second tracker including three markers config- ured to generate optical signals and a non-optical sensor configured to generate non-optical signals; and a navigation system in communication with the control system and including at least one optical sensor, wherein the navigation system is configured to:

receive, with the optical sensor, the optical signals from one or more of the three markers;

receive the non-optical signals from the non-optical sensor; and based on the received optical and non-optical signals, communicate position data indicative of a position of the anatomy to the control system to control the robotic device for cutting of the anatomy.

2. The surgical system of claim 1, wherein the navigation system is configured to determine positions of each of the three markers based on the received optical and non-optical signals.

3. The surgical system of claim 2, wherein the optical sensor is configured to receive the optical signals sequentially from the three markers, and wherein the navigation system is further configured to:

determine a position of a first of the three markers at a first time based on a first optical signal from the first marker;

determine a position of a second and third of the three markers at the first time based on the first optical signal and the non-optical signal from the non-optical sensor; and correlate the determined positions of the first, second, and third markers to the object to track the position of the anatomy.

4. The surgical system of claim 3, wherein the optical sensor receives no optical signals from the second and third markers at the first time.

5. The surgical system of claim 3, wherein the navigation system is further configured to determine the position of the second and third markers by calculating a first velocity of the first marker based on the first optical signal and by calculating velocities of the second and third markers based on the first velocity and the non-optical signal at the first time.

6. The surgical system of claim 2, wherein the navigation system is further configured to:

determine the positions of each of the three markers in a localizer coordinate system based on the optical signals and the non-optical signals; and perform a matching algorithm to match the determined positions of one or more of the markers in the localizer coordinate system with positions of the one or more of the markers in a model of the second tracker established relative to a tracker coordinate system to obtain a transformation matrix to transform the tracker coordinate system to the localizer coordinate system.

7. The surgical system of claim 2, wherein the navigation system is further configured to:

determine if one or more of the three markers is blocked from line-of-sight with the optical sensor thereby creating a blocked condition;

track a time of the blocked condition;

determine a position error tolerance associated with the one or more blocked markers;

determine a position error associated with the one or more blocked markers based on the time of the blocked condition;

determine if the position error is within the position error tolerance, and place the navigation system in an error condition if the position error exceeds the position error tolerance.

8. The surgical system of claim 1, wherein the navigation system communicates position data indicative of the position of the anatomy to the control system to further control cutting of the anatomy relative to a boundary predefined relative to the anatomy.

9. The surgical system of claim 8, wherein the cutting tool has a working end and wherein the navigation system is configured to:

monitor whether the working end of the cutting tool removes a target volume of material defined by the boundary; or determine if the working end of the cutting tool exceeds the boundary and, in response, instruct the control system to stop the cutting tool from cutting.

10. The surgical system of claim 1, wherein the navigation system communicates position data indicative of the position of the anatomy to the control system to further control cutting of the anatomy relative to a tool path defined relative to the anatomy.

11. The surgical system of claim 1, wherein the robotic device is further defined as a robotic manipulator comprising one or more arms and comprising a plurality of actuators for moving the one or more arms to move the cutting tool in at least five degrees of freedom.

12. The surgical system of claim 1, wherein the robotic device is further defined as a robotic instrument comprising a hand-held housing that is manually supported and positioned by the hand of a surgeon and a plurality of actuators configured to move the cutting tool relative to the hand-held housing.

13. A method of operating a surgical system comprising a robotic device configured to support a cutting tool and to move the cutting tool in at least three degrees of freedom, a control system configured to command the robotic device to control or constrain movement of the cutting tool, a first tracker configured to be coupled to the robotic device, a second tracker configured to be coupled to an anatomy and the second tracker including three markers configured to generate optical signals and a non-optical sensor configured to generate non-optical signals, and a navigation system in communication with the control system and including at least one optical sensor, the method comprising:

receiving, with the optical sensor of the navigation system, the optical signals from one or more of the three markers;

receiving, with the navigation system, the non-optical signals from the non-optical sensor; and based on the received optical and non-optical signals, communicating, with the navigation system, position data indicative of a position of the anatomy to the control system to control the robotic device for cutting of the anatomy.

14. The method of claim 13, further comprising the navigation system determining positions of each of the three markers based on the received optical and non-optical signals.

15. The method of claim 12, further comprising the optical sensor receiving the optical signals sequentially from the three markers, and the navigation system further:

determining a position of a first of the three markers at a first time based on a first optical signal from the first marker;

determining a position of a second and third of the three markers at the first time based on the first optical signal and the non-optical signal from the non-optical sensor; and correlating the determined positions of the first, second, and third markers to the object to track the position of the anatomy.

16. The method of claim 15, further comprising the optical sensor receiving no optical signals from the second and third markers at the first time.

17. The method of claim 15, further comprising the navigation system determining the position of the second and third markers by calculating a first velocity of the first marker based on the first optical signal and by calculating velocities of the second and third markers based on the first velocity and the non-optical signal at the first time.

18. The method of claim 14, further comprising the navigation system:
determining the positions of each of the three markers in a localizer coordinate system based on the optical signals and the non-optical signals; and
performing a matching algorithm to match the determined positions of one or more of the markers in the localizer coordinate system with positions of the one or more of the markers in a model of the second tracker established relative to a tracker coordinate system to obtain a transformation matrix to transform the tracker coordinate system to the localizer coordinate system.

19. The method of claim 14, further comprising the navigation system:
determining if one or more of the three markers is blocked from line-of-sight with the optical sensor thereby creating a blocked condition;
tracking a time of the blocked condition;
determining a position error tolerance associated with the one or more blocked markers;
determining a position error associated with the one or more blocked markers based on the time of the blocked condition;
determining if the position error is within the position error tolerance, and
placing the navigation system in an error condition if the position error exceeds the position error tolerance.

20. The method of claim 13, further comprising the navigation system communicating position data indicative of the position of the anatomy to the control system to further control cutting of the anatomy relative to a boundary predefined relative to the anatomy.

21. The method of claim 20, wherein the cutting tool has a working end and further comprising the navigation system:
monitoring whether the working end of the cutting tool removes a target volume of material defined by the boundary; or
determining if the working end of the cutting tool exceeds the boundary and, in response, instruct the control system to stop the cutting tool from cutting.

22. The method of claim 13, further comprising the navigation system communicating position data indicative of the position of the anatomy to the control system to further control cutting of the anatomy relative to a tool path defined relative to the anatomy.

23. A navigation system adapted for a robotic device configured to support a cutting tool and to move the cutting tool in at least three degrees of freedom, and the navigation system being in communication with a control system configured to command the robotic device to control or constrain movement of the cutting tool, and the navigation system comprising:
at least one optical sensor;
a first tracker configured to be coupled to the robotic device;
a second tracker configured to be coupled to an anatomy and the second tracker including three markers configured to generate optical signals and a non-optical sensor configured to generate non-optical signals; and
a computing system including at least one processor configured to:
receive, with the optical sensor, the optical signals from one or more of the three markers;
receive the non-optical signals from the non-optical sensor; and
based on the received optical and non-optical signals, communicate position data indicative of a position of the anatomy to the control system to enable the control system to control the robotic device for cutting of the anatomy.

* * * * *